(12) United States Patent
Hepp et al.

(10) Patent No.: US 10,041,878 B2
(45) Date of Patent: Aug. 7, 2018

(54) METHOD FOR MEASURING AND DETERMINING A TERAHERTZ SPECTRUM OF A SAMPLE

(71) Applicant: BRUKER OPTIK GmbH, Ettlingen (DE)

(72) Inventors: Christian Hepp, Gaggenau (DE); Stephan Luettjohann, Karlsruhe (DE)

(73) Assignee: Bruker Optik GmbH, Ettlingen (DE)

( * ) Notice: Subject to any disclaimer, the term of this patent is extended or adjusted under 35 U.S.C. 154(b) by 0 days.

(21) Appl. No.: 15/495,251

(22) Filed: Apr. 24, 2017

(65) Prior Publication Data
US 2017/0307520 A1 Oct. 26, 2017

(30) Foreign Application Priority Data
Apr. 25, 2016 (DE) .................. 10 2016 206 965

(51) Int. Cl.
G01J 5/02 (2006.01)
G01N 21/3581 (2014.01)
G01N 21/39 (2006.01)

(52) U.S. Cl.
CPC ......... *G01N 21/3581* (2013.01); *G01N 21/39* (2013.01)

(58) Field of Classification Search
CPC .... G01N 21/3581; G01N 21/49; G01N 21/59; G01N 21/3563; G01N 21/3577
See application file for complete search history.

(56) References Cited

U.S. PATENT DOCUMENTS

| | | | |
|---|---|---|---|
| 7,876,803 B1* | 1/2011 | Di Teodoro | H01S 3/06791 372/10 |
| 8,482,739 B1* | 7/2013 | Wanke | G01J 3/0256 250/341.1 |

(Continued)

OTHER PUBLICATIONS

Roggenbuck A. et al., "Coherent broadband continuous-wave terahertz spectroscopy on solid-state samples", New Journal of Physics 12, (2010), 14 pages.

(Continued)

*Primary Examiner* — Kiho Kim
(74) *Attorney, Agent, or Firm* — Edell, Shapiro & Finnan, LLC

(57) ABSTRACT

A method for measuring and determining a THz spectrum of a sample (17) having an improved spectral resolution. Two laser beams (1a, 2a) are superimposed, such that two parts (11, 12) of a superimposed laser radiation are generated, which have a beat frequency in the THz range. The first part (11) is introduced into an emitter (13) for generating a THz radiation (14), which passes through the sample. The characteristic transmission radiation (18) thus obtained is forwarded to a detector (15), which is activated by the second part (12) of the superimposed laser radiation. By repetition with different beat frequencies, a measurement signal I(f) of the form $I(f)=A(f)\cos[\Phi(f)]$ is obtained for the sample. An auxiliary signal $\tilde{I}(f)$ shifted by 90° is determined from the measurement signal I(f), with $\tilde{I}(f)=A(f)\cos[\Phi(f)\pm 90°]$. The THz spectrum S(f) of the sample is determined by the auxiliary signal $\tilde{I}(f)$, with $S(f)=|z(f)|=|I(f)+i\tilde{I}(f)|$.

12 Claims, 11 Drawing Sheets

(56) References Cited

U.S. PATENT DOCUMENTS

| | | | | |
|---|---|---|---|---|
| 2004/0155665 A1* | 8/2004 | Arnone | .............. | G01N 21/3581 |
| | | | | 324/644 |
| 2005/0100866 A1* | 5/2005 | Arnone | ................ | A61B 5/0088 |
| | | | | 433/215 |
| 2006/0049356 A1* | 3/2006 | Shen | .................. | G01N 21/1717 |
| | | | | 250/341.1 |
| 2006/0255277 A1* | 11/2006 | Cole | ......................... | G01J 3/42 |
| | | | | 250/341.1 |
| 2008/0151239 A1* | 6/2008 | Iketaki | ................... | G01N 21/41 |
| | | | | 356/317 |
| 2009/0009855 A1* | 1/2009 | Nakatsuka | .......... | H01S 3/06716 |
| | | | | 359/343 |
| 2010/0321767 A1* | 12/2010 | Borguet | ................ | G02F 1/3544 |
| | | | | 359/330 |

OTHER PUBLICATIONS

Roggenbuck A. et al., "Using a fiber stretcher as a fast phase modulator in a continuous wave terahertz spectrometer", Optical Society of America, Apr. 2012, vol. 29, No. 4, pp. 614-620.

Lu, Zheng et al. "Study of terahertz LFMCW imaging radar with Hilbert transform receiver", Electronics Letters, Mar. 2014, vol. 50, No. 7, pp. 549-550.

\* cited by examiner

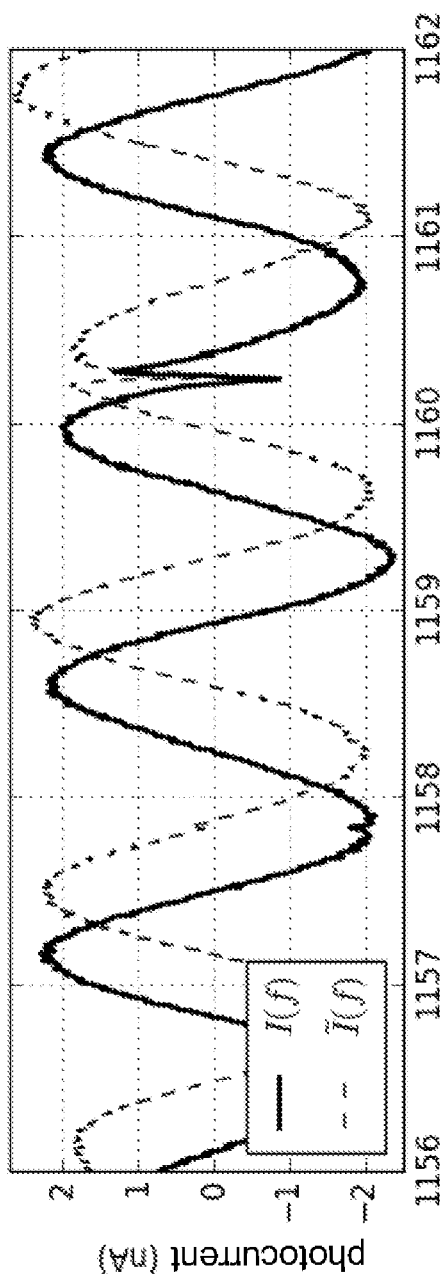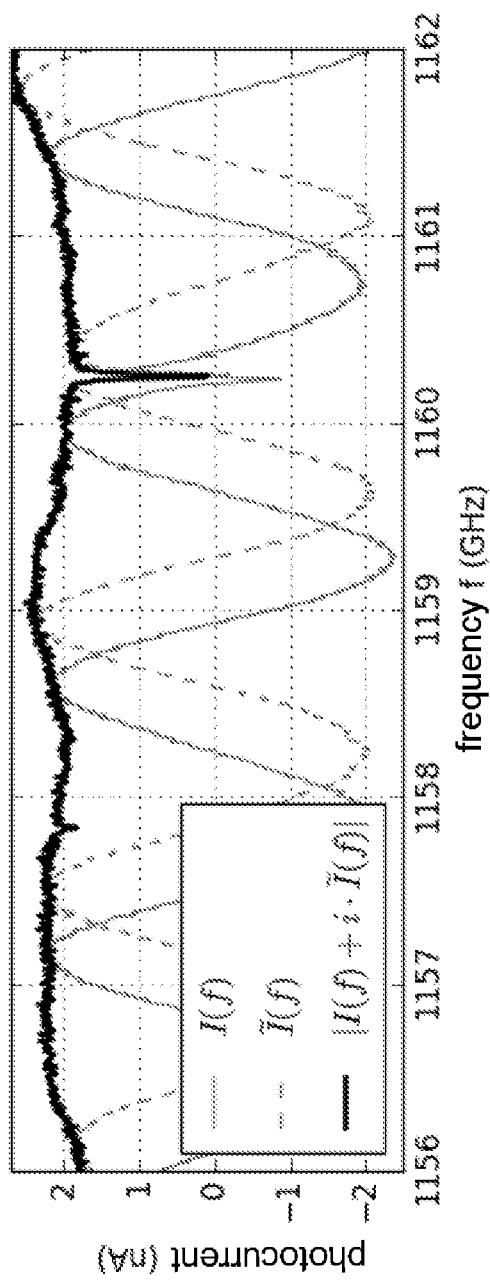

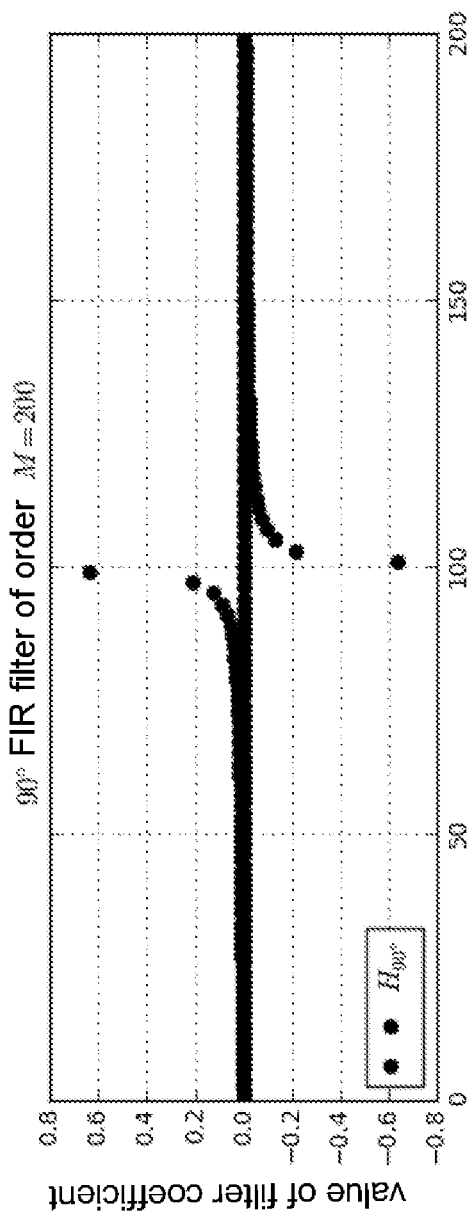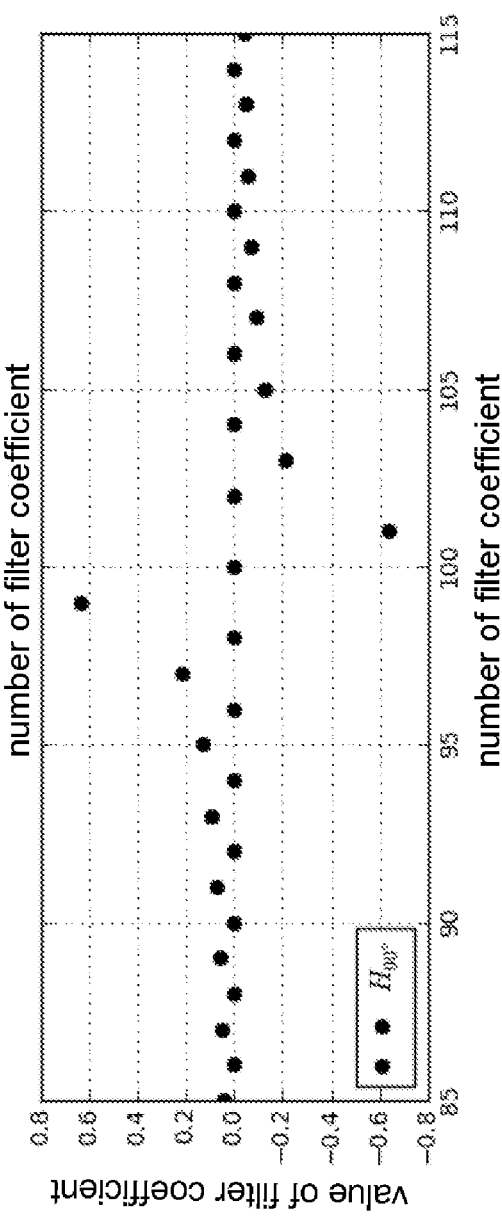

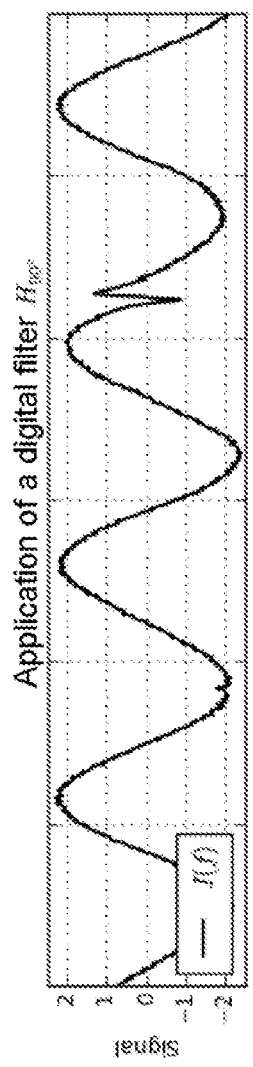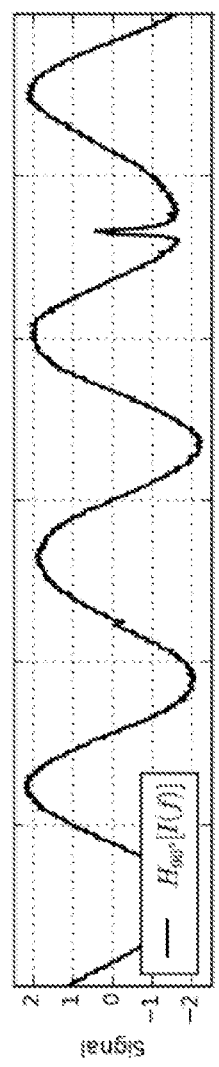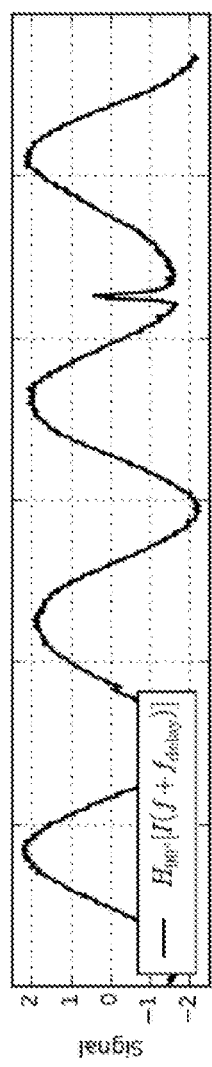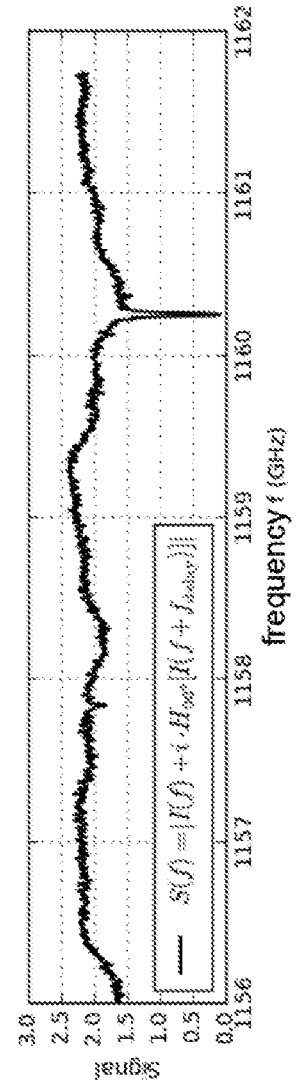

METHOD FOR MEASURING AND DETERMINING A TERAHERTZ SPECTRUM OF A SAMPLE

The invention relates to a method for measuring and determining a THz spectrum of a sample.

Such a method has been disclosed by A. Roggenbuck et al., New Journal of Physics 12 (2010), 043017 (13pp), hereinafter reference [2].

Samples, in particular gaseous samples in a measuring cell, can be characterized by means of terahertz (THz) spectroscopy.

The generation and detection of THz radiation is experimentally difficult.

Usually, the laser radiation of two lasers that have slightly different laser frequencies $f_1$, $f_2$ is superimposed. The superimposition causes a beat having a beat frequency corresponding to the frequency difference $\Delta f$, which is in the THz range. A first part of the superimposed laser radiation is sent to a THz transmitter, which correspondingly emits THz radiation. This THz radiation is guided through a sample, as a result of which a characteristic interaction occurs, and the transmitted radiation is detected at a receiver. The THz radiation can be tuned by varying the laser frequencies f1 and/or f2.

The receiver has to be activated by a second part of the superimposed laser radiation. As a result, the signal (photocurrent) $I(\omega)$ at the receiver is proportional to the product of the two parts of the superimposed laser radiation such as they arrive at the detector taking into account optical path differences and the interaction with the sample, with:

$$I(\omega) = A(\omega) \cdot \cos\left(\frac{l_1 - l_2}{c} \cdot \omega - \varphi(\omega)\right)$$

with $\omega = 2\pi f$ angular frequency of the THz radiation; $l_1$, $l_2$ optical path lengths of the parts of the superimposed laser radiation, $\varphi(\omega)$ phase shift depending on the sample, $A(\omega)$ frequency-dependent amplitude depending on the sample; c: speed of light. The photocurrent $I(\omega)$ is successively measured (scanned) over a multiplicity of individual angular frequencies $\omega$.

The measured photocurrent $I(\omega)$ has an oscillation on account of the cosine term. Only the determination of $A(\omega)$ is relevant for the determination of an absorption spectrum of the sample. The phase $$\Phi(\omega) = \frac{l_1 - l_2}{c} \cdot \omega - \varphi(\omega)$$

depends on the dispersion of the sample and on the optical path length difference between the two parts of the superimposed laser radiation.

In order to deduce the frequency-dependent amplitude $A(\omega)$ from the photocurrent $I(\omega)$ without knowledge of the phase term $\varphi(\omega)$, in which in particular the dispersion of the sample has an influence, it is possible to evaluate the curve $I(\omega)$ only at its extreme points, cf. reference [2]. At these points, $\cos(\omega)$ is in each case 1 or −1. The associated so-called envelope of the photocurrent $I(\omega)$ is relatively simple to determine but has a significantly coarser frequency pattern than the photocurrent $I(\omega)$. Data points of the photocurrent $I(\omega)$ which are not at an extremum are omitted, and, accordingly, no amplitude $A(\omega)$ is then available even at the associated angular frequencies $\omega$.

The coarser frequency pattern of the envelope can have the effect that narrowband absorption lines such as they occur for instance in gases at low pressure can no longer be resolved.

In A. Roggenbuck et al., J. Opt. Soc. Am. B, vol. 29, No. 4, April 2012, pages 614-620, referred to hereinafter as reference [1], it is proposed, at a respective angular frequency $\omega$, to vary the path length difference between the first part and the second part of the superimposed laser radiation by means of fiber stretchers. Over a period, the maximum and the minimum of the photocurrent are then also gone through, as a result of which the amplitude $A(\omega)$ can be determined for the associated angular frequency $\omega$. Reference [1] indicates that signal averaging over approximately 240 periods is carried out. With this method the amplitude $A(\omega)$ can be determined at all angular frequencies, but the measurement set-up becomes very complex as a result of the fiber stretchers and the measurement duration becomes very long owing to the required tuning of the path length difference at each measurement frequency.

OBJECT OF THE INVENTION

The invention is based on the object of providing a method for measuring and determining a THz spectrum in which an improved spectral resolution can be achieved in a simple manner.

BRIEF DESCRIPTION OF THE INVENTION

This object is achieved by means of a method for measuring and determining a THz spectrum of a sample, comprising a) generating a first laser beam having a frequency $f_1$ and a second laser beam having a frequency $f_2$, with $f_2 > f_1$ and with $f_1$, $f_2$ in the visible or near-infrared spectral range, wherein both laser beams are superimposed in a beam splitter, in particular fiber-based beam splitter, for forming a superimposed laser radiation having a beat frequency $fs = f_2 - f_1$ in the THz range and said superimposed laser radiation is available at the two outputs of the beam splitter, b) converting a first part of the superimposed laser radiation behind a first output of the beam splitter at an emitter into THz radiation and transmitting said THz radiation through a sample, as a result of which a characteristic transmission radiation is obtained, c) radiating the characteristic transmission radiation onto a detector whose detectivity is determined by a second part—radiated onto the detector—of the superimposed laser radiation behind a second output of the beam splitter, such that a measurement value I(fs) is obtained at the detector, d) repeating steps a) to c) a number of times with n different beat frequencies fs, such that a discrete frequency-dependent measurement signal I(f) is obtained, in particular at the beat frequencies $f[k] = k \cdot \delta f + f_0$, with $k = 1, \ldots, n$ and $f_0$: starting frequency, wherein the measurement signal I(f) is of the form $I(f) = A(f) \cdot \cos[\Phi(f)]$ with A(f): amplitude term, and $\Phi(f)$: phase term, e) determining an auxiliary signal $\tilde{I}(f)$ shifted by 90° from the measurement signal I(f), with $\tilde{I}(f) = A(f) \cdot \cos[\Phi(f) \pm 90°]$, f) determining the THz spectrum S(f) by means of the auxiliary signal $\tilde{I}(f)$, with $S(f)=|z(f)|=|I(f)+i\tilde{I}(f)|$.

The invention proposes determining an auxiliary signal $\tilde{I}(f)$ from the measured measurement signal or photocurrent I(f), where the auxiliary signal is phase-shifted by 90° (or π/2) relative to the photocurrent I(f), but is otherwise identical, in particular with regard to the amplitude. This can be carried out by means of Hilbert transformation, for example. By means of the signals I(f) and $\tilde{I}(f)$ it is then easily possible to determine the absolute value $|I(f)+i\tilde{I}(f)|=\sqrt{[I(f)]^2+[\tilde{I}(f)]^2}$ (with i: imaginary unit) for all frequencies f in each case, which corresponds to the amplitude A(f) or to the spectrum S(f).

In this case, the spectrum S(f) can be determined with all measurement points or frequencies f, in particular even for measurement points between the extreme points of the photocurrent curve. As a result, with the same frequency pattern of the generated THz radiation that is guided through the sample and measured, it is possible to achieve a better resolution than in the case where the evaluation of the photocurrent curve is restricted to the extreme points. In particular, even narrow absorption lines between the extreme points of the photocurrent curve can be detected and resolved.

The method can furthermore be carried out with a conventional experimental set-up in which only the beat frequency for the different measurement points need be tuned. It is not necessary to tune the phase for each measurement point by means of a change in the optical path length difference; in other words, in particular no fiber stretchers are required. The measurement signal I(f) or the spectrum S(f) can be measured in a relatively short time.

The first and second laser beams are in the visible spectral range (approximately 400 nm to 800 nm, or $7.5*10^{14}$ Hz to $3.75*10^{14}$ Hz) or else in the near-infrared spectral range (approximately 800 nm to 3000 nm or $3.75*10^{14}$ Hz to $1.0*10^{14}$ Hz); the THz radiation is typically in a frequency range of 200 GHz ($2*10^{11}$ Hz) to 5 THz ($5*10^{12}$ Hz), and preferably between 300 GHz and 3 THz. The sample is typically present in gaseous form in a gas cell.

PREFERRED VARIANTS OF THE INVENTION

In one preferred variant of the method according to the invention, in step e) the auxiliary signal $\tilde{I}(f)$ is determined from the measurement signal I(f) by applying a Hilbert transformation, with $\tilde{I}(f)=H[I(f)]$. By means of the Hilbert transformation, the cosine term of the photocurrent I(f) or I(ω) (with ω=2πf) is converted into a sine term, as a result of which the desired phase difference of 90° is obtained in a simple manner.

Furthermore, in one advantageous variant, in step e) the following substeps are applied:
i) applying a complex Fourier transformation to the measurement signal I(f), such that a transformed measurement signal I(t) in the time domain is obtained,
ii) applying a filter function to the transformed measurement signal I(t), such that a filtered transformed measurement signal GEF[I(t)] is obtained,
iii) applying the inverse complex Fourier transformation to the filtered transformed measurement signal GEF[I(t)], such that a complex inverse-transformed measurement signal RUC(f) is obtained, the imaginary part of which is used as $\tilde{I}(f)$.

This procedure makes it possible to form the auxiliary signal $\tilde{I}(f)$ in a simple manner by means of (discrete) Fourier transformation and inverse Fourier transformation. This procedure is very accurate, moreover, since it derives the auxiliary signal from the entire measurement signal (with all frequencies). It should be noted that the inverse-transformed signal once again contains the signal of the photocurrent I(f) as real part. Either the original measurement signal of the photocurrent or the real part of the inverse-transformed signal can be used for the calculation of |z(f)|.

Preference is given to a development of the above variant in which a vector h of the length n is used as filter function, with
a. $h_i=1$ for i=1 and for $$i=\frac{n}{2}+1$$

b. $h_i=2$ for $$i=2,3,\ldots,\frac{n}{2}$$

c. $h_i=0$ for $$i=\frac{n}{2}+2,\ldots,n$$

for n even, and
a'. $h_i=1$ for i=1 and for i=n/2+½
b'. $h_i=2$ for $$i=2,3,\ldots,\frac{n}{2}-1/2$$

c'. $h_i=0$ for i=n/2+3/2, . . . , n
for n odd,
wherein the vector h is multiplied element by element by the transformed measurement signal I(t). The transformed measurement signal I(t) comprises "positive" and "negative" times. These filter functions cut off half of the times (for instance the negative times) in the transformed measurement signal I(t), as a result of which a desired phase offset of 90° is generated.

Furthermore, in one advantageous variant of the method according to the invention, this variant provides that in step e) the auxiliary signal $\tilde{I}(f)$ is approximately determined by means of a digital filter, wherein the digital filter is applied step by step in each case only to a continuous portion of the measurement values of the measurement signal I(f), in order to determine a respective individual value of the auxiliary signal $\tilde{I}(f)$ whose frequency occurs in the continuous portion of the measurement values. This variant makes it possible, even during the measurement of the measurement signal l(f), already to begin with the calculation of the auxiliary signal $\tilde{I}(f)$ or to obtain corresponding parts of the spectrum S(f). In particular, it is not necessary, for the determination of data points of the auxiliary signal $\tilde{I}(f)$ or associated parts of the spectrum S(f), firstly to wait for the recording of the entire measurement signal I(f), that is to say for all frequencies f. The continuous portion is typically a specific number of measurement points (e.g. twenty), that were measured last. For applying the digital filter to the measurement signal, the following specifications are applicable:

for the filter (of order M) a real-valued vector H(f) exists which describes the impulse response of the filter in the frequency domain.

The filter is applied to the measurement signal I(f) by way of the following specification: $H[I(f)]=\Sigma_{k=0}^{M-1} H(k) \cdot I(f-k)$. The result of the calculation is written into a (real) vector H[I(f)].

The digital filter H approximates the formation of the Hilbert transform H[I(f)], that is to say that it shifts the phase of the input signal I(f) by 90° and ideally does not change the amplitude of the input signal. In addition, it causes a delay of the signal H[I(f)] relative to I(f).

Said delay is compensated for or canceled by means of suitable methods, such that I(f) and H[I(f)] are identical apart from the 90° phase shift.

Forming the complex vector $z(f)=I(f)+i\ H[I(f)]$.

Further method corresponding to step f) of the main claim, wherein H[I(f)] here corresponds to $\tilde{I}(f)$.

The following properties hold true for the digital filter H:

the filter is completely defined by way of its response function $\tilde{H}(t)$ (in the time domain, i.e. in the conjugate domain with respect to the frequency domain in which the measurement signal I(f) is present), from which the amplitude and phase response functions $A_H(t)=|H(t)|$ and $\varphi_H(t)=\arg(H(t))$, respectively, can be calculated.

The amplitude response function $A_H(t)$ is ideally $A_H(t)=1$ for all positive times t>0 and $A_H(t)=0$ for t≤0.

The phase response function $\varphi_H(t)$ is ideally 90° plus a linear component, i.e. $\varphi_H(t)=\pm 90°+\text{const}\cdot t$, wherein const is a constant.

In an alternative variant of the method according to the invention, it is provided that in step e), instead of $\tilde{I}(f)$ a z(f) is approximately determined as $H_1[I(f)]+iH_2[I(f)]$, wherein $H_1$, $H_2$ are digital filters, wherein the digital filters are applied step by step in each case only to an identical, continuous portion of the measurement values of the measurement signal I(f), in order to determine a respective individual value of z(f) whose frequency occurs in the continuous portion of the measurement values, with $H_1[I(f)]=A(f)\cdot\cos[\Phi(f)+\alpha]$ and $H_2[I(f)]=A(f)\cdot\cos[\Phi(f)\pm 90°+\alpha]$, with α: phase offset of the digital filterings, and wherein in step f) determining the THz spectrum S(f) is carried out not by means of the auxiliary signal $\tilde{I}(f)$, but rather with $S(f)=|z(f)|=|H_1[I(f)]+iH_2[I(f)]|$. This variant makes it possible, even during the measurement of the measurement signal I(f), already to begin with the calculation of z(f) or once again to obtain corresponding parts of the spectrum S(f). In particular, it is not necessary, for the determination of data points of z(f) or corresponding parts of the spectrum s(f), firstly to wait for the recording of the entire measurement signal I(f), that is to say for all frequencies f. The continuous portion is typically a specific number of measurement points (e.g. twenty) that were measured last.

For applying the filters $H_1$ and $H_2$ to the measurement signal, the following specifications are applicable:

for the filters there exist real-valued vectors $H_1(f)$ and $H_2(f)$, which describe the impulse response of the filter in the frequency domain.

The filters are applied to the measurement signal I(f) in each case by way of the formula $H_{1,2}[I(f)]=\Sigma_{k=0}^{M-1}H_{1,2}(k)\cdot I(f-k)$. The results of the calculation are written into two (real) vectors $H_{1,2}[I(f)]$.

The filters $H_1$ and $H_2$ are configured such that they change the amplitude of the measurement signal to exactly the same extent, and that, when applied to I(f), they generate a relative phase shift of 90° between $H_1[I(f)]$ and $H_2[I(f)]$.

In addition, $H_1$ and $H_2$ cause the same delay on the signals $H_1[I(f)]$ and $H_2[I(f)]$, such that $H_1[I(f)]$ and $H_2[I(f)]$ are identical apart from the 90° phase shift. In both signals, the common delay is canceled.

Forming the complex vector $z(f)=H_1[I(f)]+i\ H_2[I(f)]$.

Further method corresponding to step f) of the main claim, wherein $H_1[I(J)]$ then corresponds to I(f) and $H_2[I(f)]$ then corresponds to $\tilde{I}(f)$.

The following properties hold true for the digital filters $H_1$ and $H_2$:

the filters are completely defined by way of their response functions $H_1(t)$ and $H_2(t)$ in the time domain, from which the amplitude and phase response functions $A_{H1,2}(t)=|H_{1,2}(t)|$ and $\varphi_{H1,2}(t)=\arg(H_{1,2}(t))$, respectively, can be calculated.

The response functions $H_1(t)$ and $H_2(t)$ of the filters $H_1$ and $H_2$ are linked to one another by the relationship $H_1(t)=-\text{sgn}(t)\cdot H_2(t)$ with the sign function sgn(t). It furthermore holds true that: $H_i(-t)=H^*_i(t)$ for i=1,2 and with the complex conjugate $H^*_i$.

For the amplitude response functions $A_{H1,2}(t)$ it ideally holds true that:

$$A_{H1,2}(t) = \begin{cases} 1 & \text{for } t < 0 \\ 0 & \text{for } t = 0 \\ 1 & \text{for } t > 0 \end{cases}$$

the phase response functions $\varphi_{H1}(t)$ and $\varphi_{H2}(t)$, for t>0, ideally have a phase difference of $\Delta\varphi(t)=|\varphi_{H1}(t)-\varphi_{H2}(t)|=90°$.

In one advantageous variant, it is provided that a THz reference spectrum $S_0(f)$ is measured and determined analogously to steps a) to f) but without a sample;

and the THz spectrum S(f) of the sample is divided element by element by the THz reference spectrum $S_0(f)$, such that a transmission spectrum $$T(f) = \frac{S(f)}{S_0(f)}$$

is obtained. In the transmission spectrum, the spectral information is attributed exclusively to the sample; background effects are removed by normalization by means of the division. As a result, the transmission spectrum is easier to interpret than the "unnormalized" THz spectrum of the sample, in particular with regard to the qualitative and quantitative composition of the sample. If the sample is arranged in a container (for instance a gas cell) whose container walls are arranged in the beam path during the measurement, the reference measurement "without a sample" should be carried out with the same container or a container of the same type in the beam path, but with said container being empty (without the container being filled with the sample).

One preferred development of this variant provides that an absorbance Abs(f) is calculated from the transmission spectrum T(f) by forming the negative common logarithm, with: $\text{Abs}(f)=-\log_{10}(T(f))$. By way of the absorbance, in a diagram absorption lines of different intensities can be better detected or discerned simultaneously.

Preference is furthermore given to a variant which provides that $I_0(f)$ and $\tilde{I}_0(f)$ are measured and determined analogously to steps a) to e), but without a sample;

and given a known sample thickness d the real part of the refractive index n(f) of the sample is determined, as a function of the frequency f, comprising the following steps:

calculating the phase $$\varphi(f) = \arctan\left(\frac{\tilde{I}(f)}{I(f)}\right)$$

for all frequency points of the variables I(f) and $\tilde{I}(f)$, determined with sample, calculating the phase $$\varphi_0(f) = \arctan\left(\frac{\tilde{I}_0(f)}{I_0(f)}\right)$$

for all frequency points of the variables $I_0(f)$ and $\tilde{I}_0(f)$, determined without sample;

calculating the phase difference $\Delta\varphi(f) = \varphi(f) - \varphi_0(f)$ for all frequencies f, and subsequently calculating the real part of the refractive index n(f) by applying the following formula:

$$n(f) = \frac{\Delta\varphi(f) \cdot c}{2\pi d f}$$

with the speed of light c.

A simple and rapid determination of the frequency-dependent refractive index or of the dispersion of the sample is possible by means of this procedure. The determination has a high resolution and does not require special experimental set-ups, in particular fiber stretchers.

Preference is likewise given to a variant which provides that $I_0(f)$ and $\tilde{I}_0(f)$ are measured and determined analogously to steps a) to e), but without a sample;

and given a known real part n(f) of the refractive index of the sample, the sample thickness d is determined, comprising the following steps:

calculating the phase $$\varphi(f) = \arctan\left(\frac{\tilde{I}(f)}{I(f)}\right)$$

for all frequency points of the variables I(f) and $\tilde{I}(f)$, determined with sample;

calculating the phase $$\varphi_0(f) = \arctan\left(\frac{\tilde{I}_0(f)}{I_0(f)}\right)$$

for all frequency points of the variables $I_0(f)$ and $\tilde{I}_0(f)$, determined without sample;

calculating the phase difference $\Delta\varphi(f) = \varphi(f) - \varphi_0(f)$ for all frequencies f;

applying the formula $$d(f) = \frac{\Delta\varphi(f) \cdot c}{2\pi n(f) f}$$

to the frequency points f, and averaging the variable d(f) over all frequencies f in order to obtain the sample thickness $d = \overline{d(f)}$.

The advantage of this variant is that $\Delta\varphi(f)$ is measured with high resolution, i.e. for many frequencies f. As a result, many points are available for the averaging and the determination of d becomes more accurate.

Preference is also given to a variant in which information about a qualitative and/or quantitative composition of the sample is determined from the THz spectrum S(f) of the sample and/or from the transmission spectrum T(f) and/or from the absorbance Abs(f). On account of the high resolution of the THz spectrum of the sample or of the variables T(f) or Abs(f) derived therefrom, it is possible to make particularly accurate statements about the sample composition. In particular, the position of absorption lines can be evaluated for the qualitative analysis, and the integral below absorption lines and/or the peak height of the absorption lines for the quantitative analysis.

Further advantages of the invention are evident from the description and the drawing. Likewise, the features mentioned above and those that will be explained still further can be used according to the invention in each case individually by themselves or as a plurality in any desired combinations. The embodiments shown and described should not be understood as an exhaustive enumeration, but rather have exemplary character for outlining the invention.

DETAILED DESCRIPTION OF THE INVENTION AND DRAWING

The invention is illustrated in the drawing and is explained in greater detail on the basis of exemplary embodiments. In the figures:

FIG. 6a shows a diagram of a THz absorption measurement, illustrating upward the photocurrent I(f) (solid line) and a 90° phase-shifted auxiliary signal $\tilde{I}(f)$ (dashed line) as a function of the frequency f plotted toward the right, according to the invention;

FIG. 6b shows the diagram from FIG. 6a, additionally with the spectrum of the sample $S(f) = |I(f) + i\tilde{I}(f)|$ (illustrated in bold), according to the invention;

FIG. 8a shows a diagram illustrating an FIR (finite impulse response filter) $H_{90°}$, for the invention, with the value of the filter coefficient plotted upward, and the number of the filter coefficient plotted toward the right;

FIG. 8b shows an extract from the diagram from FIG. 8a, in the region around the number of the filter coefficient k=100;

FIG. 9a shows a diagram of a THz absorption measurement, illustrating upward the measurement signal (photocurrent) I(f) as a function of the frequency f plotted toward the right;

FIG. 9b shows the diagram from FIG. 9a, after application of the FIR filter $H_{90°}$ to I(f), according to the invention;

FIG. 9c shows the diagram from FIG. 9a, after application of the FIR filter $H_{90}$ to the measurement signal $I(f+f_{delay})$ with phase shift $f_{delay}$, according to the invention, FIG. 9d shows the diagram from FIG. 9a, after the determination of the spectrum $S(f)=|I(f)+i\cdot H_{90°}[I(f+f_{delay})]|$, according to the invention;

1. BACKGROUND OF THE INVENTION a) Overview of the Procedure in the Prior Art

In order to determine a THz spectrum, the photocurrent I(f) is measured which has oscillations on account of the measuring method used. The THz spectrum is given by the amplitude A(f) of this oscillating photocurrent.

Hitherto, the amplitude A(f) and thus the THz spectrum has been compiled from the absolute values of the maxima $I(f_{max})$ at the points $f=f_{max}$ and from the absolute values of the minima $I(f_{min})$ at the points $f=f_{min}$.

As a result, the spectral resolution of the THz spectrum is limited to the oscillation period of the photocurrent measurement curve.

b) Measurement Set-Up for THz Spectra and Properties of the Photocurrent

Firstly, the measurement set-up for detecting the measurement signal [photocurrent I(f)] will be explained. Such a measurement set-up is also used for the method according to the invention, and the method according to the invention uses a measurement signal determined by such a measurement set-up.

Figure 1:
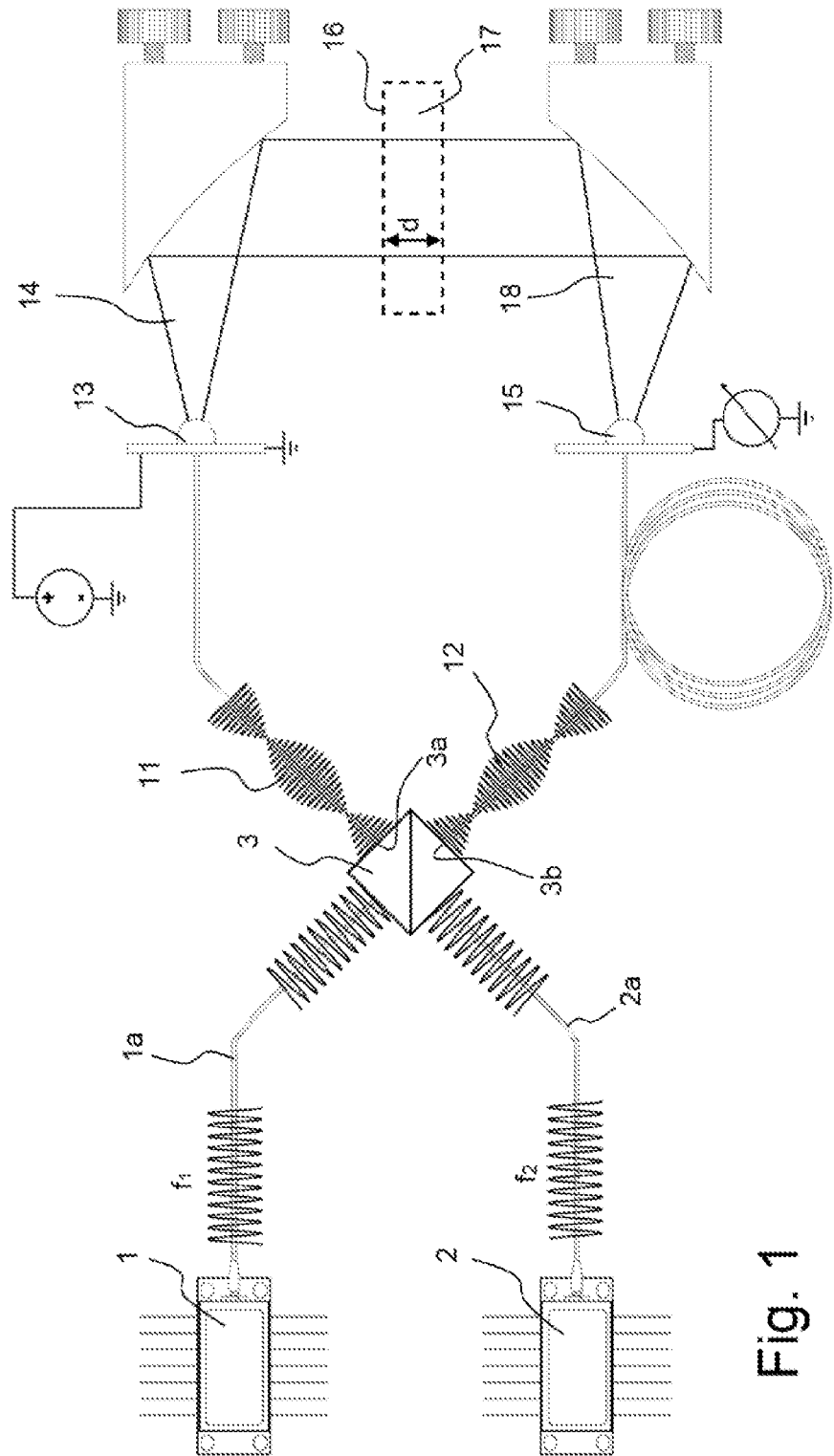
FIG. 1 shows a schematic overview of the set-up of a THz spectrometer, for the method according to the invention.

FIG. 1 schematically illustrates a typical measurement set-up of a THz spectrometer. In order to generate the THz radiation, firstly two lasers 1, 2, which are operated at slightly different frequencies $f_1$, $f_2$, are mixed on a fiber-based 50/50 beam splitter 3. The wavelength of the lasers 1, 2 is unimportant a priori (it is usually approximately 1500 nm), but what is important is the frequency difference $\Delta f=f_1-f_2$ or $\Delta\omega=\omega_1-\omega_2$ with $\omega=2\pi f$ (hereinafter, reference is made primarily to the angular frequency $\omega$). The frequency difference of the lasers 1, 2 is in the region of one terahertz, and can be varied by detuning the lasers 1, 2 with respect to one another. Upon the superimposition of the (coherent) laser beams 1a, 2a of the lasers 1, 2 at the beam splitter 3, cf. the first part 11 and the second part 12 of the superimposed laser radiation, a beat (laser beat) arises, wherein the envelope of the beat oscillates precisely with the frequency difference $\Delta f$ of the two lasers 1, 2. This beat frequency is thus likewise in the terahertz range.

Behind the 50/50 beam splitter 3 the (now superimposed) laser beams are transmitted firstly (cf. the first part 11) to the emitter (THz transmitter) 13, where a THz radiation 14 is generated. Secondly (cf. the second part 12), the laser beams are transmitted to the detector (THz receiver) 15.

In the transmitter 13 (also referred to as Tx for short), as a result of the incident laser signal (that is to say the first part 11), charge carriers are excited to oscillate. However, on account of their mobility, said charge carriers can only follow the low frequency given by the envelope. Since the envelope oscillates at THz frequency, an electromagnetic wave is thus generated which has the angular frequency $\omega_{THz}=\Delta\omega$ (hereinafter, the subscript "THz" will be dispensed with in the case of the frequency $\omega$). This THz wave then passes through a sample compartment 16 and is focused onto the receiver 15. In the beam path or in the sample compartment 16 (formed by a gas cell, for instance) it is possible to position a sample 17 (in particular a gaseous sample) having a thickness d whose spectral properties (transmission/absorption) are of interest; as a result, the THz radiation 14 becomes a characteristic transmission radiation 18.

The receiver 15 (also referred to as Rx for short) is a semiconductor-based detector which can be "armed to detection" as a result of the incidence of laser radiation. If it is impinged on by the laser beam arriving from the left in FIG. 1 (that is to say the second part 12), it is able to measure the field of the incident THz wave. In this case, the detected signal (that is to say the photocurrent I(f)) is proportional both to the electric field of the arriving laser beam $E_{Rx}^{Laser}(t, z)$ and to the electric field $E_{Rx}^{THz}(t, z)$ of the THz wave at the location of the detector 15, that is to say that the photocurrent I(f) is proportional to the product of the two fields:

$$I \propto E_{Rx}^{THz}(t,z) \cdot E_{Rx}^{Laser}(t,z) \qquad (1)$$

Figure 2:
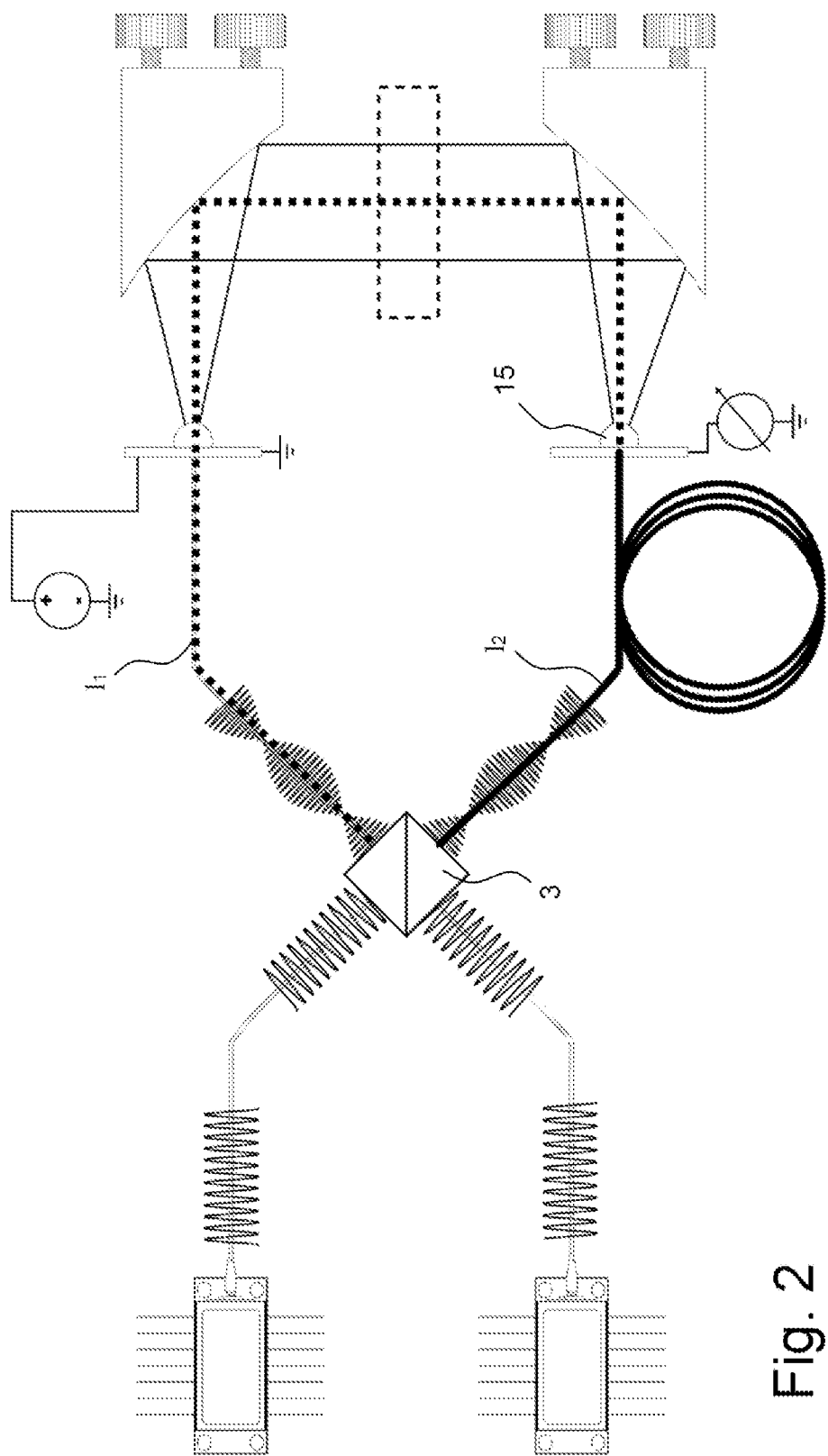
FIG. 2 shows the THz spectrometer from FIG. 1, with identification of the path lengths of the first part and the second part of the superimposed laser radiation.

On the path to the detector 15, the two fields pick up different phases $\varphi_1$, $\varphi_2$ on their different paths from the photomixer (beam splitter 3) since they traverse different optical path lengths $l_1, l_2$. These two lengths $l_1, l_2$ are illustrated as dotted and solid curves in FIG. 2. The set-up is similar to an interferometer having two arms of different lengths, but in the present case the fields are multiplied by one another, rather than being added together as in the case of an interference experiment.

Both laser field and THz field can be written in a simplified way as a plane wave of frequency $\omega$, wherein the laser traverses precisely the path length $z=l_2$ and the THz wave traverses the path length $z=l_1$:

$$E_{Rx}^{THz}(t,z=l_1) \propto \cos(\omega t - \varphi_1) \qquad (2a)$$

$$E_{Rx}^{Laser}(t,z=l_2) \propto \cos(\omega t - \varphi_2) \qquad (2b)$$

The photocurrent then results as:

$$I \propto \cos(\omega t - \varphi_1) \cdot \cos(\omega t - \varphi_2) \quad (3)$$

Using a cosine multiplication rule this expression can be simplified as:

$$I \propto \cos(\varphi_1 - \varphi_2) + \cos(2\omega t - \varphi_1 - \varphi_2). \quad (4)$$

The second term oscillates with the frequency $2\omega$. This frequency is too fast to be able to be detected by the electronics; the term thus averages to zero. The first term is a DC component that can be measured. The phase difference $\varphi_1 - \varphi_2$ can be expressed as:

$$\varphi_1 - \varphi_2 = \frac{l_1 - l_2}{c} \cdot \omega. \quad (5)$$

That is to say that the phase difference is dependent on the THz frequency and the path length difference. In order to determine a spectrum $S(\omega)$ [or $S(f)$], the frequency $\omega$ is detuned and the path length difference in this case is left constant apart from the influence of the dispersion. The phase difference $\varphi_1 - \varphi_2$ thus changes. The detected photocurrent therefore oscillates with the change in the phase difference.

$$I(\omega) \propto \cos\left(\frac{l_1 - l_2}{c} \cdot \omega\right) \quad (6)$$

The period of this oscillation is given by $c/(l_1-l_2)$, that is to say that if the two path lengths are very similar, $l_1 \approx l_2$, then the oscillation of the photocurrent has a very long period as a function of the chosen terahertz frequency. Conversely, if the path lengths are very different, then the photocurrent oscillates very rapidly as a function of the terahertz frequency.

If a sample 17 is additionally introduced into the beam path, then equation (6) has to be modified. Introducing a sample 17 having the thickness d into the beam path may for example affect the amplitude of the radiation as a result of absorption of radiation, and affect the phase as a result of the refractive index n of the sample 17. Equation (6) therefore has to be supplemented by a frequency-dependent amplitude term $A(\omega)$ and an additional phase $\varphi(\omega)$ resulting from the dispersion of the sample 17. The photocurrent is obtained as a function of the THz frequency:

$$I(\omega) = A(\omega) \cdot \cos\left(\frac{l_1 - l_2}{c} \cdot \omega - \varphi(\omega)\right) \quad (7)$$

For this phase term it holds true that:

$$\varphi(\omega) = \frac{nd}{c} \cdot \omega \text{ with } n = n(\omega) \quad (8)$$

A change in the oscillation period of the photocurrent $I(\omega)$ follows from the dispersion. The optically denser medium of the sample 17 lengthens one of the two partials beams 11, 12 (here partial beam 11) in the set-up.

Figure 3:
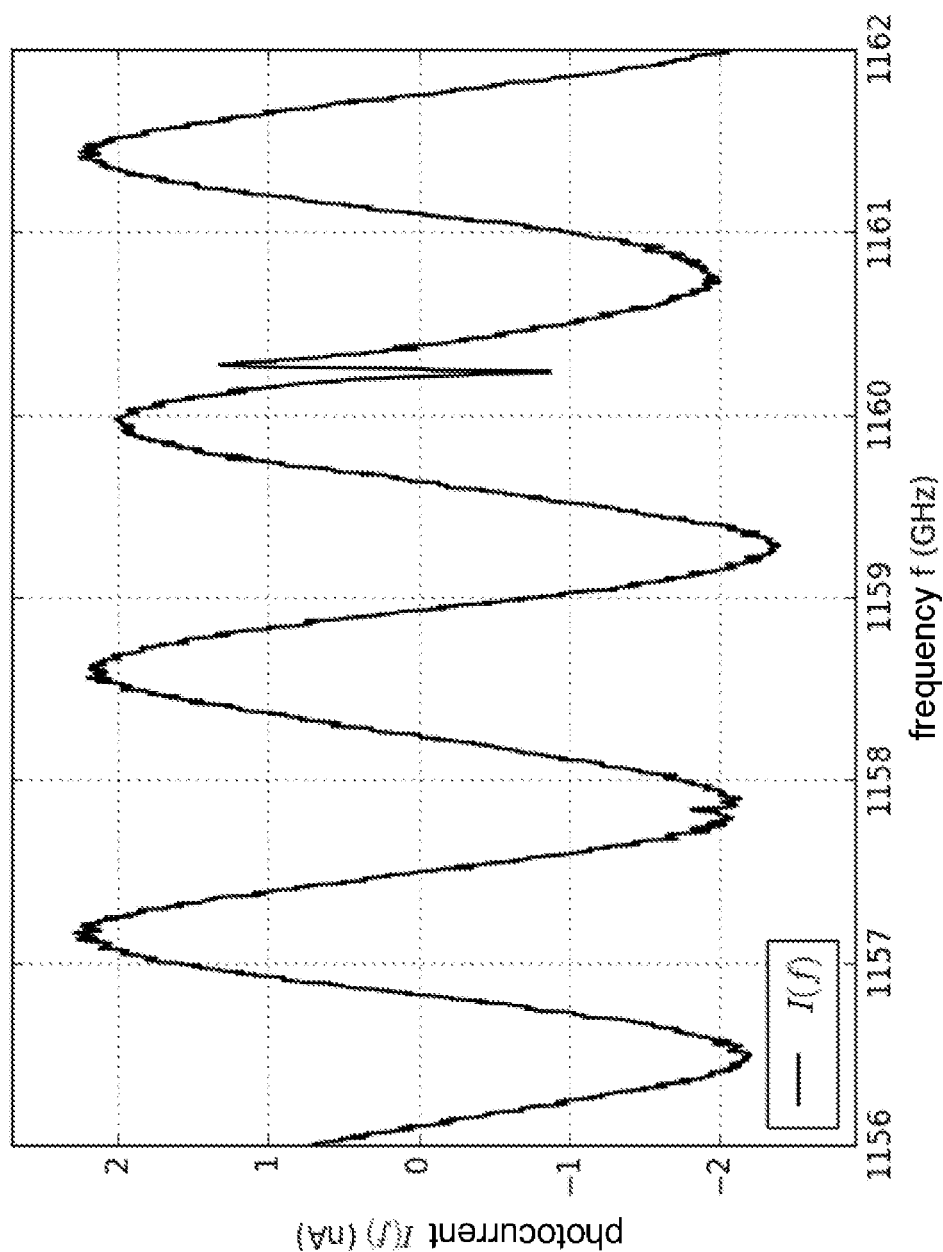
FIG. 3 shows a diagram of a THz absorption measurement with a sample in a gas cell, with the photocurrent I(f) plotted upward and the frequency f plotted toward the right.

The photocurrent I(f) during a typical measurement with a gas cell is illustrated in FIG. 3. The absorption of the terahertz radiation during passage through a gas cell was examined during the measurement. The spectral feature ("dip") in the right-hand region of the curve (at approximately 1160 GHz), is important; it arises due to an absorption line of water. The line is spectrally narrowband since a low gas pressure was used in the gas cell.

The following section shows that this spectral feature is not adequately resolved by the prior art.

c) Determining the Amplitude According to the Prior Art

The method of data evaluation according to the prior art will now be described, and the limitation that arises as a result will be explained.

The functional dependence of the photocurrent on the THz frequency $\omega$ is given by equation (7). This equation contains the amplitude $A(\omega)$ and the phase $\varphi(\omega)$ as frequency-dependent variables. Both variables have to be determined from the measurement curve, only the amplitude $A(\omega)$ being relevant for the determination of an absorption spectrum (of the "absorbance"). The determination of two unknowns from only one measurement curve is a non-trivial, inverse problem since at every point of the curve it is necessary to determine two variables from one equation.

Hitherto (cf. reference [2]), the amplitude $A(\omega)$ was determined at the maxima $\omega = \omega_{max}$ and minima $\omega = \omega_{min}$, of the curve $I(\omega)$ since it is known at these points that the argument of the cosine is the even and respectively odd multiple of $\pi$:

$$\frac{l_1 - l_2}{c} \cdot \omega_{max} - \varphi(\omega_{max}) = n \cdot 2\pi, \quad (9a)$$

$n = 0, 1, 2, \ldots$ for maxima and $$\frac{l_1 - l_2}{c} \cdot \omega_{min} - \varphi(\omega_{min}) = (2m+1) \cdot \pi, \quad (9b)$$

$m = 0, 1, 2, \ldots$ for minima

Figure 4:
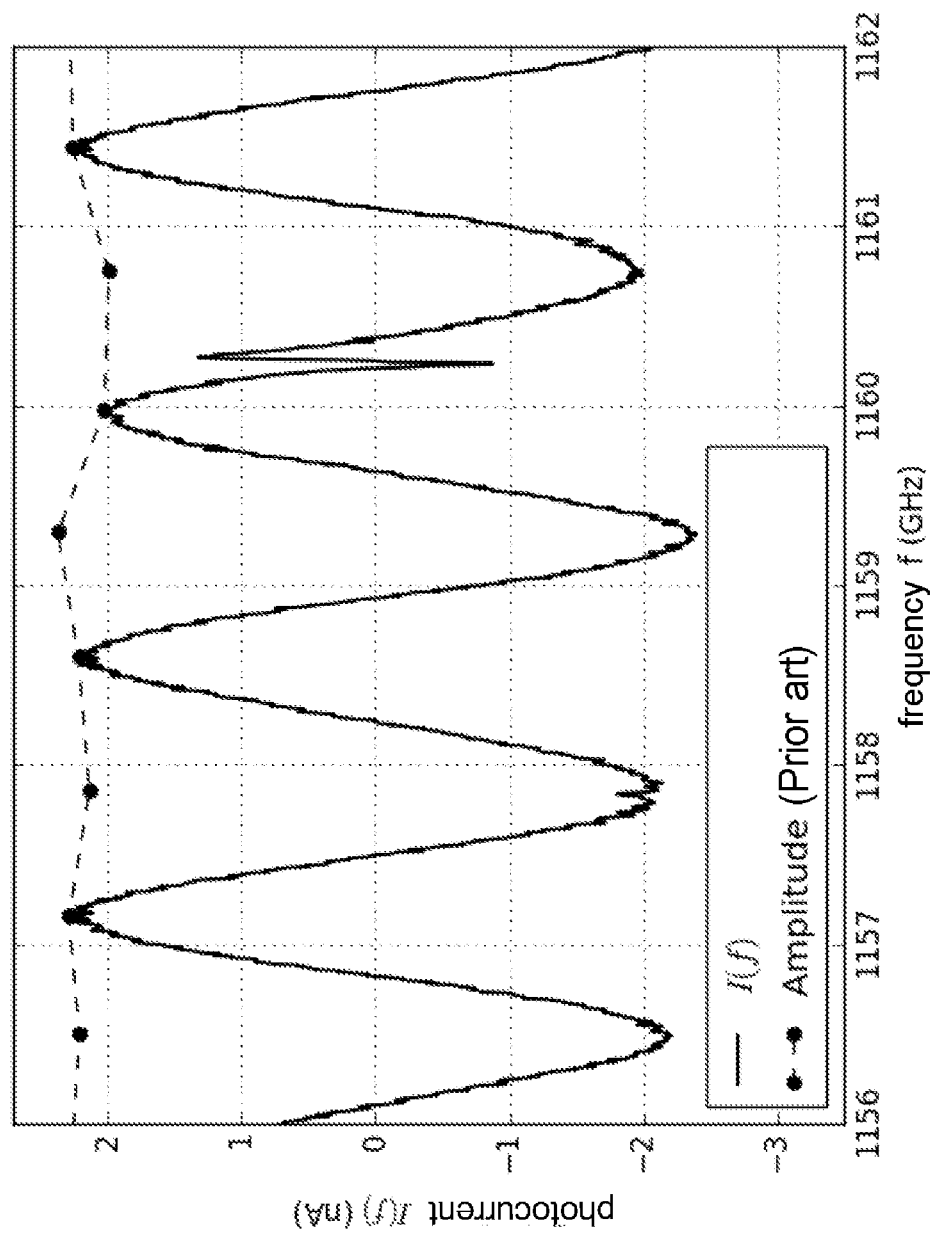
FIG. 4 shows the diagram from FIG. 3, with an envelope determined according to the prior art, with non-resolved dip.

Thus, at these points the determination of the phase $\varphi(\omega)$ is obviated (since the cosine results here in each case as 1 or as −1) and the determination of $A(\omega)$ is unambiguous. A corresponding calculation can be integrated into the measurement software, and the result $A(\omega_{min/max})$ thereof is also referred to as the "envelope". FIG. 4 shows an amplitude curve determined in such a way according to the prior art (circles linked by dashed line). It is evident that the amplitude curve calculated in this way contains only few points, and the above-described dip in the right-hand part of the curve of the photocurrent I(f) is not resolved in the envelope.

Figure 5:
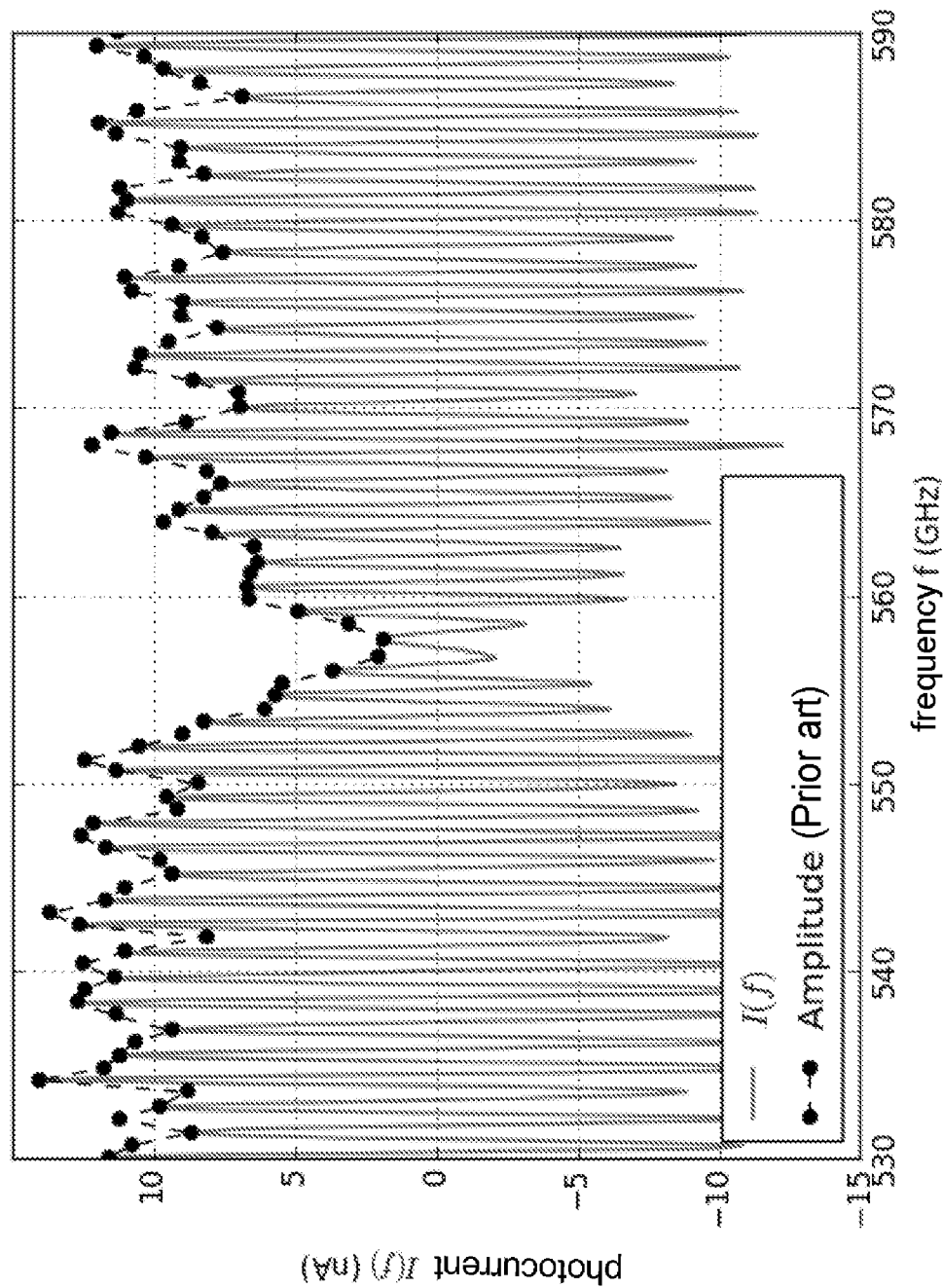
FIG. 5 shows a diagram of a THz absorption measurement with a sample in a gas cell, with the photocurrent I(f) plotted upward and the frequency f plotted toward the right, with an envelope determined according to the prior art in the case of a broadband absorption.

If the absorption dip were wider than the distance between multiple extrema, then the limited resolution would not be a problem. Such an example is illustrated in FIG. 5. In the center of the spectrum it is observed that the photocurrent dips over a width of approximately 5 GHz that is to say that the oscillations have a significantly smaller amplitude. In this case, too, an absorption line of water vapor is involved, but this line was measured at high pressure. As a result of the high pressure, so-called collisional broadening occurs and the absorption line has a significantly higher linewidth than in FIG. 3 and FIG. 4. The absorption line in FIG. 5 extends over approximately oscillations in the photocurrent and can thus be resolved by the conventional determination of the envelope (amplitude curve, circles linked by dashed line).

d) On the Definition of the Term "Resolution" in the Evaluation of the Photocurrent Curve Hereinafter, repeated use is made of the term "resolution" in comparative form ("higher resolution" and "lower resolution"). It is therefore expedient to define the term in the context of the determination of the amplitude A(f) of the photocurrent I(f).

Let there be a periodically oscillating photocurrent in accordance with eq. (7). This photocurrent curve is measured for discrete frequency values $f_i$ (with i: counting index). We assume that within a period $p=c/(l_1-l_2)$ of the photocurrent curve there are m measurement values with the spacing $\delta f=|f_{i+1}-f_i|$. With the evaluation according to the prior art, two points for the amplitude curve are obtained within a period—one point for the maximum within the period and one point for the minimum. Hereinafter, these points are called "result points" r. The spectral resolution capability $\Delta f$ using the method in accordance with the prior art (with r=2) is thus $$\Delta f = \frac{p}{r} = \frac{m \cdot \delta f}{2},$$

and is related directly to the oscillation period p (also see the following section). In order that the oscillation can be identified as such, there should be a sufficient number of data points between a minimum and a neighboring maximum. The more data points there are therebetween, the more accurately the extremum points can be identified, that is to say that for the spacing of the measurement values $\delta f$ it holds true that: $\delta f \ll p=c/(l_1-l_2)$. As a consequence, it is necessary to measure the photocurrent curve in steps of $\delta f$, but the evaluation method according to the prior art yields only a resolution $\Delta f$, that is coarser by the factor m/2. If it were desired to improve the resolution capability, then firstly the oscillation period p must be reduced (also see the following section). At the same time, however, the step size $\delta f$ must also be decreased in order to correctly detect the oscillation. If the intention is to pass through the same spectral range as before, then the total number of measured points of the measurement increases. A fixed integration time is required for each measurement point; the time requirement of a measurement thus increases.

As will be shown later, in the case of the present invention the resolution is limited only by the step size $\delta f$; therefore, for the same time requirement, the invention offers a resolution improved by the factor m/2.

e) Relationship Between Evaluation Method and Physical Set-Up of the Measurement As represented above in equations (6) and (7), the oscillation period of the photocurrent is proportional to the path length difference $l_1-l_2$. In the concrete experiment, this path length difference is set by the length of the optical fibers between beam splitter and transmitter and receiver, respectively. In a typical experimental set-up, by way of example, the path length difference is $l_1-l_2\approx21$ cm, which leads to an oscillation period of $$p = \frac{c}{l_1 - l_2} = 1.4 \text{ GHz}.$$

If the evaluation method described above is then used, and the extremum points are used in the calculation of the amplitude of the photocurrent, data points are obtained with a resolution of 0.7 GHz (the minima are also taken into account, that is to say that by seeking the maxima of the absolute value of the photocurrent, data points with the spacing from a maximum to the adjacent minimum are thus obtained). That means that the resolution is directly coupled to the "physical configuration of the set-up" (of the fiber length chosen). If there is a desire to change the possible resolution, then the configuration must be changed, and the evaluation method thus has a repercussion on the experiment. This repercussion is eliminated in the context of the invention.

f) Targeted Alteration of the Optical Path Length for Controlling the Phase $\varphi(\omega)$ Reference [1] describes an instrumental technology which can be used as an alternative to the evaluation technique shown above and which makes it possible to determine the amplitude $A(\omega)$ for all the measurement points $\omega$. In the case of this technology, a so-called fiber stretcher is incorporated into the optical fiber connecting the beam splitter to the THz transmitter or respectively to the receiver. With said fiber stretcher, the optical fiber is mechanically elongated and the optical path length $l_1$ or respectively $l_2$ is thus altered in a targeted manner. In the case of a change in the path length $l_1$, for instance, the argument of the cosine in equation (7) can be rewritten as $$\frac{l'_1 - l_2}{c} \cdot \omega - \varphi(\omega),$$

where $l'_1 = l_1 + l_{fiber}$,
wherein $l_{fiber}$ is the set additional length of the fiber. The length of the $l_{fiber}$ can be set in a targeted manner for each measurement point $\omega$; $l_{fiber}$ thus becomes a function of the frequency $l_{fiber}(\omega)$. It is instructive to consolidate the term $l_{fiber}(\omega)$ with the frequency-dependent phase $\varphi(\omega)$:

$$\frac{l_1 - l_2}{c} \cdot \omega + \underbrace{\frac{l_{fiber}(\omega)}{c} \omega - \varphi(\omega)}_{=\tilde\varphi(\omega)},$$

that is to say that the use of the fiber stretcher leads to a control of the phase $\tilde\varphi(\omega)$. By way of example, it is then possible to set $\tilde\varphi(\omega)$ for each frequency $\omega$ such that the argument of the cosine is always precisely an integer multiple of $2\pi$ and the cosine term in equation (7) always yields 1:

$$I(\omega) = A(\omega) \cdot \underbrace{\cos\left(\frac{l_1 - l_2}{c} \cdot \omega - \tilde\varphi(\omega)\right)}_{=1} = A(\omega).$$

The determination of the amplitude $A(\omega)$ is thus unambiguous for every measurement point and the limitation to the extremum points of the photocurrent curve is obviated.

Reference [1] explains that the alteration of the fiber length is applied periodically, that is to say that the phase $\tilde\varphi(\omega)$ is varied periodically between 0 and $2\pi$. The precise procedure in [1] is not set out exactly; the authors write that the photocurrent is determined at the receiver by averaging the signal.

Although the method using the fiber stretcher is not subject to the limitations of the evaluation method described above, the method entails the following disadvantages:
 an additional component (fiber stretcher) with a high cost factor has to be integrated into the set-up.
 The phase $\tilde\varphi(\omega)$ has to be varied for each measurement point $\omega$; the measurement time is lengthened as a result.

With the method according to the invention, the use of a fiber stretcher is not necessary, as a result of which the experimental set-up is simplified, and a variation of the phase for each measurement point or each measurement frequency ω is not required, as a result of which the measurement time is shortened.

2. MEASUREMENT AND DETERMINATION OF A THz SPECTRUM ACCORDING TO THE INVENTION a) Overview According to the invention, the amplitude $A(\omega)$ is calculated for every data point in the oscillating photocurrent, not just for the extremum points. By means of the measurement signal (photocurrent) $I(f)$, an auxiliary signal $\tilde{I}(f)$ phase-shifted by 90° is formed. The absolute value of the amplitude $A(f)$ or the spectrum $S(f)$ can then be determined for all frequencies f from $$|I(f)+i\tilde{I}(f)|=\sqrt{[I(f)]^2+[\tilde{I}(f)]^2}.$$

Preference is given to the following possibility for determining the amplitude: the calculation of the analytical signal is used. A complex number $z(f)=x(f)+i\cdot y(f)$ (i: imaginary unit) is formed from the measurement signal (photocurrent curve $I(f)$). In this case, the real part $x(f)$ is equal to the photocurrent curve $I(f)$, and the imaginary part is equal to the Hilbert transform $X[I(f)]$ of the photocurrent curve $I(f)$. From the complex absolute value $|z(f)|$, a value of the amplitude $A(f)$ is obtained for each frequency f of the measurement curve.

Thus, in the determination of the amplitude there is no limitation to the period of the extremum points $f_{min/max}$, and a higher spectral resolution is thus achieved for the amplitude and thus for the spectrum.

b) Description of One Preferred Variant for Determining the Spectrum $S(f)$ by Means of a Fourier Transformation Let there be a photocurrent curve as a function of the frequency f [cf. equation (7)]:

$$I(f) = A(f) \cdot \cos\left(\frac{2\pi f}{p} + \varphi(f)\right) + A_0 \quad (10)$$

In this case, $A(f)$ is the frequency-dependent amplitude of the measurement signal, $\omega(f)$ is the frequency-dependent phase and $p=c/(l_1-l_2)$ is the oscillation period of the photocurrent. A possible constant offset $A_0$ is disregarded ($A_0=0$). The amplitude $A(f)$ of the measurement signal is sought.

In order to calculate the amplitude, the following algorithm is used in the variant presented here:
1. Take the real-valued measurement signal (photocurrent) $I(f)$ and form the discrete, complex Fourier transformation (DFT or FFT). Store the result in a (complex) vector v. The vector v has the length n, as does the output signal $I(f)$ as well. For simplification, it shall be assumed here that n is even.
2. Form a vector h having the same length as the vector v. The elements $h_i$ of h have the following values:
 $h_i=1$ for $i=1$ and for $$i = \frac{n}{2} + 1$$

$h_i=2$ for $$i = 2, 3, \ldots, \frac{n}{2}$$

$h_i=0$ for $$i = \frac{n}{2} + 2, \ldots, n$$

3. Calculate the product of h and v element by element.
4. Calculate the inverse, discrete and complex Fourier transform (IDFT or IFFT) of the product of h and v just calculated.
 The result of this inverse FFT is the complex vector $z(f)=I(f)+i\tilde{I}(f)$ having the original measurement signal $I(f)$ as real part and having the Hilbert transform $\tilde{I}(f)=[I(f)]$ as imaginary part. The complex vector $z(f)$ is also referred to as analytical signal.
5. Form the complex absolute value $s(f)=|z(f)|$; the latter corresponds to a good approximation to the amplitude $A(f)$ sought, i.e. $s(f)\approx A(f)$.
 The approximation referred to in point 5 consists in the fact that the calculated amplitude $S(f)$ at the edges of the measurement range (<5 oscillation periods) has artifacts in relation to the actual amplitude $A(f)$.

c) Advantages of the Method According to the Invention

According to the invention, the amplitude $A(f)$ is determined for each measurement point f—therefore, it is also possible to speak of the instantaneous envelope or current envelope.

FIG. 6a and FIG. 6b illustrate the calculation of the amplitude $A(f)$ and instantaneous envelope according to the method according to the invention for the photocurrent curve from FIG. 3. Proceeding from the original measurement signal $I(f)$, by means of the method described above (steps 1-4), an auxiliary signal $\tilde{I}(f)$ (illustrated in a dashed fashion), phase-shifted by 90°, of the signal $I(f)$ (illustrated in a solid fashion) is calculated (FIG. 6a). On the basis of these two curves, the analytical signal $z(f)=I(f)+i\tilde{I}(f)$ is calculated, whose absolute value $|z(f)|$ (illustrated in bold) corresponds to the instantaneous envelope $A(f)$ (FIG. 6b).

Figure 7:
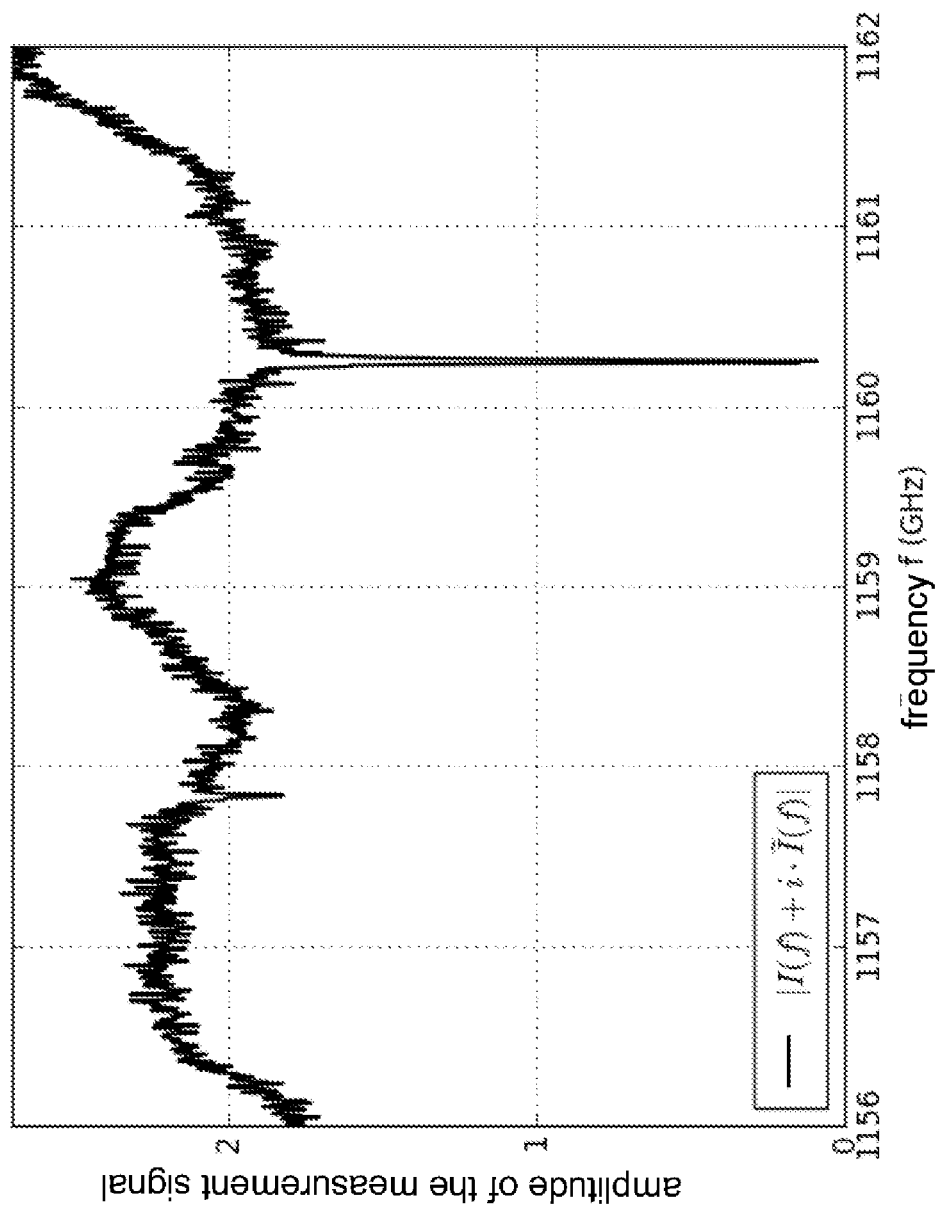
FIG. 7 shows an enlarged detail of the spectrum of the sample $S(f)=|I(f)+i\ \tilde{I}(f)|$ from FIG. 6b, in the region of the peak at approximately 1160 GHz.

It is evident that the instantaneous envelope—as before—nestles smoothly against the maxima of the photocurrent curve. In contrast to the previous method, however, in the case of the method according to the invention, the calculated amplitude curve $A(f)$ has exactly the same number of measurement points as the original photocurrent curve. This leads to an improvement in the spectral resolution in comparison with the previous method. In the right-hand half of the spectrum it is evident that the absorption line is resolved even in the amplitude curve. For a better overview, FIG. 7 once again illustrates the amplitude curve $A(f)$ without the photocurrent curves in the region around the peak at approximately 1160 GHz as an enlarged detail with respect to FIG. 6b (y-axis is scaled to relevant region).

d) Resolution Capability of the Method According to the Invention

It was shown above that in the case of the calculation of the amplitude curve in accordance with the prior art (without a fiber stretcher) a spectral resolution capability of $\Delta f=p/2$ is possible, wherein $p=m\cdot\delta f$ corresponds to an oscillation period of the photocurrent that is scanned with m steps of step size $\delta f$. Using the method according to the invention, the resolution capability Δf corresponds precisely to the step size δf, since the amplitude curve in the case of the method according to the invention contains exactly the same number of points as the photocurrent curve. Given identical measurement parameters, therefore, the resolution capability is improved by the factor m/2 in comparison with the conventional method.

e) Alternative Formation of the Hilbert Transform

The variant shown above uses the formation of the Fourier transformation for calculating the Hilbert transform or the analytical signal. In order that this method can be applied, the measurement signal I(f) must be present for the entire measurement range, that is to say all relevant frequencies f. Furthermore, the calculated amplitude curve A(f) becomes all the more accurate, the wider the chosen measurement range. That means that during the ongoing measurement the amplitude curve can be calculated only with inadequate accuracy.

Therefore, hereinafter a number of alternatives are shown which can be used to calculate the Hilbert transform H or the analytical signal z(f) without using the Fourier transformation. These methods are directly applicable to the measurement signal I(f), such that the amplitude curve A(f) can be calculated during the ongoing measurement.

f) Use of a Hilbert Transformer

In these alternative methods, predefined, discrete filter curves H(f) ("digital filters") are applied to the measurement signal I(f). The filter H(f) is present as a finite impulse response (FIR) filter of order M, and is applied to the measurement signal I(f) by way of the so-called difference equation (it should be noted that the measurement points are discrete frequencies f with step size δf):

$$H[I(f)] = \sum_{k=0}^{M-1} H(k) \cdot I(f - \delta f \cdot k) \quad (11)$$

A first approach involves creating the impulse response H(f) such that by applying H[I(f)] of the filter to the measurement signal I(f) the Hilbert transform x[I(f)] is approximated, that is to say that the filtering H[I(f)] generates a signal Ĩ(f) that differs from I(f) ideally only in a 90° phase shift. Such a filter H is also called a Hilbert transformer. The complex vector z(f)=I(f)+i Ĩ(f) is then constructed from I(f) and Ĩ(f), the amplitude |z(f)| being calculated from said complex vector as above.

representation H(f) in the frequency domain has a simple analytical expression.

In order to realize a Hilbert transformation, the filter in the present case is constructed such that H̃(t) is similar to a bandpass filter, that is to say that |H̃(t)| has a rectangular shape. The passband of the filter ideally includes all positive times (t>0) and the stop band ideally includes all negative times (t<0). Since the measurement signal I(f) consists of n discrete measurement points with spacing δf, the Fourier transform F[I(f)] of the measurement signal extends only over the range of from $-(\delta f)^{-1}$ to $+(\delta f)^{-1}$ with a point spacing of $(n\cdot\delta f)^{-1}$. It suffices to define finite, upper and lower limits for the passband of the filter H̃(t). The lower limit for the passband is then $t_L \approx (n\cdot\delta f)^{-1}$, and the upper limit is $t_H \approx (2\delta f)^{-1}$. The impulse response H(f) of the filter for such a form of H̃(t) corresponds approximately to the form $\sin^2(f)/f$, but the concrete functional form of H(f) depends on the choice of various factors, such as e.g. the filter type or the parity of the filter length (even/odd number of points).

In addition to the phase shift of 90°, the digital filter has a constant group delay time, different from zero, which causes an additional delay $f_{delay}$ of the filtered signal H[I(f)]. That means that the application of the filter first of all generates H[I(f)]=Ĩ(f−$f_{delay}$). The delay $f_{delay}$ depends on the length of the filter and is thus a known variable. It is possible simply to shift the frequency axis of the complex variable Ĩ by the value $-f_{delay}$, that is to say that H[I(f+$f_{delay}$)] and thus Ĩ(f−$f_{delay}$)→Ĩ(f) are formed. The analytical signal z(f)=I(f)+i Ĩ(f) is subsequently constructed from the curves I(f) and Ĩ(f).

The concept of a digital filter implies that the measurement signal to which the filter is applied is present in discrete points distributed equidistantly. In the case of the measuring method according to the invention, the photocurrent I(f) can be determined in discrete frequency steps $f=f_k=\delta f \cdot k+f_0$ with index k=0, . . . , n, step size δf and starting frequency $f_0$, that is to say that it then meets this condition. A filter $H_{90°}$ is defined analogously thereto in discrete steps which are a priori independent of the frequency values f. In order to clarify this circumstance, hereinafter we write the impulse response H(k) as a function of the variable k=0, 1, . . . , M−1. The quantity M denotes the order of the filter and corresponds to the length of the filter. Applying the filter to the measurement curve (with step size δf) then yields a relationship between the length (the so-called order) of the filter and the width thereof in the frequency domain. In the design

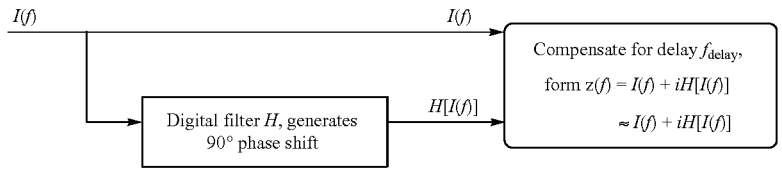

The filter H(f) is constructed in advance as a real-valued vector. In this case, the filter is unambiguously defined by way of its Fourier transformation H̃(t)=F[H(f)] in the time domain, that is to say that the functional profile of H̃ depending on time t is defined. Between the representation in the time domain and the representation in the frequency domain, there is then an unambiguous relationship by way of the inverse Fourier transformation. It is customary to construct the function H̃(t) in the time domain such that the of the filter it is important to note that the filter order M of $H_{90°}$ corresponds approximately to the order of magnitude of the period length p of the periodic measurement signal.

Example Regarding the Application of a Hilbert Transformer

To illustrate the method, an FIR filter $H_{90°}$ of the order M=200 is constructed, that is to say that the filter has a length of 200 filter coefficients. The filter coefficients are calculated in accordance with the function $$H(k) = \begin{cases} 0, & \text{for } k = \frac{M}{2} \\ \frac{\sin^2\left(\frac{\pi}{2}\left(\frac{M}{2}-k\right)\right)}{\frac{\pi}{2}\left(\frac{M}{2}-k\right)}, & \text{otherwise} \end{cases} \quad (12)$$

The impulse response $H_{90°}(k)$ of the 90° FIR filter that results from equation (12), for use as a Hilbert transformer, is illustrated in FIG. 8a and in an enlarged extract in the region around k=100 in FIG. 8b. It is evident that every second filter coefficient is equal to zero.

When the filter is applied to the data set shown below (cf. FIG. 9a), the filter order M corresponds approximately to a spectral width of 0.8 GHz, and is thus of the same order of magnitude as the oscillation period p=1.4 GHz of the photocurrent I(f).

The FIR filter $H_{90°}$ defined in FIGS. 8a and 8b is then applied to the measurement signal I(f) from FIG. 3 in accordance with equation (11). The application of the FIR filter $H_{90°}$ to a photocurrent curve I(f) (illustrated in FIG. 9a) leads to the 90° phase-shifted, delayed curve $H_{90°}[I(f)]$ (illustrated in FIG. 9b). In order to remove the delay, the curve is shifted by the frequency $f_{delay}$ (as illustrated in FIG. 9c), and the instantaneous envelope S(f) is calculated as absolute value |z(f)| of the analytical signal $z(f)=I(f)+i·H_{90°}[I(+f_{delay})]$ (see FIG. 9d).

It is evident in FIG. 9d that, as a result of the application of $H_{90°}$, the amplitude curve A(f) can likewise be reconstructed with high accuracy. No significant deviations can be discerned in a direct comparison with the variant according to the invention shown above (using the Fourier transformation).

g) Use of a Phase Splitter

The central property of the analytical signal $z(f)=I(f)+i$ $\tilde{I}(f)$ is that there is a phase difference of 90° between real part I(f) and imaginary part $\tilde{I}(f)$; apart from this phase shift, however, the portions are otherwise identical. In the approach shown above, the Hilbert transformer H was used in order to generate this 90° phase shift on the measurement signal I(f). This involves an asymmetrical method in which the phase shift is present in the imaginary part $\tilde{I}(f)$ and the real part $\tilde{I}(f)$ is identical to the original signal. As a further alternative approach, it is possible to use a symmetrical filter method in which both real part and imaginary part of the analytical signal z(f) are processed using two separate filters $H_1$, $H_2$ ("digital filters"). Once again the aim of this filtering is that there is a phase difference of 90° between real and imaginary parts, but the amplitudes of the portions are identical. The filters $H_1$, $H_2$ in interaction are also referred to as a phase splitter.

As in the previous approach, $H_1$ and $H_2$ are constructed such that—applied together—they act as a bandpass filter, and once again it is expedient to define the properties of the filters in the Fourier domain, i.e. for $\tilde{H}_1(t)$ and $\tilde{H}_2(t)$. In this case, it holds true that $\tilde{H}_1(t) = -i·\text{sgn}(t)·\tilde{H}_2(t)$, with the sign function sgn(t). Furthermore, it holds true that $H_i(-t)=H^*_i(t)$ for i=1,2 and with the complex conjugate $H^*_i$. It follows from these conditions that the amplitude responses $|\tilde{H}_1(t)|$ and $|\tilde{H}_2(t)|$ of the filters $H_1$ and $H_2$ are identical, and that there is a phase difference $\Delta\varphi(t)=|\varphi_{H_1}(t)-\varphi_{H_2}(t)|=90°$ between the response functions $\tilde{H}_1(t)$ and $\tilde{H}_2(t)$, wherein $$\varphi_{H1}(t) = \arctan\left(\frac{\Im[\tilde{H}_1(t)]}{\Re[\tilde{H}_1(t)]}\right),$$

analogously for $\varphi_{H2}(t)$. Ideally, for the amplitude responses it holds true that $$|\tilde{H}_i(t)| = \begin{cases} 1 & \text{for } t < 0 \\ 0 & \text{for } t = 0, \\ 1 & \text{for } t > 0 \end{cases}$$

once again for i=1,2.

The impulse responses $H_1(f)$ and $H_2(f)$ of the filters $H_1$ and $H_2$ in the frequency domain are generated by applying the discrete, inverse Fourier transformation to $\tilde{H}_1(t)$ and $\tilde{H}_2(t)$, respectively:

$$H_1(f) = \mathcal{F}^{-1}[\tilde{H}(t)] \text{ and } H_2(f) = \mathcal{F}^{-1}[\tilde{H}(t)]$$

The impulse responses $H_1(f)$ and $H_2(f)$ are applied, as before, directly to the measurement signal I(f). Analogously to the Hilbert transformer H in the previous approach, $H_1$ and $H_2$ generate an additional delay of the signal I(f). This delay is identical for $H_1$ and $H_2$, and it can be corrected in a similar manner to the previous approach. However, the delay is not constant for all times t, such that a small artifact (so-called Chirp) remains during the correction of the delay.

Example Regarding the Application of a Phase Splitter

Figure 10A:
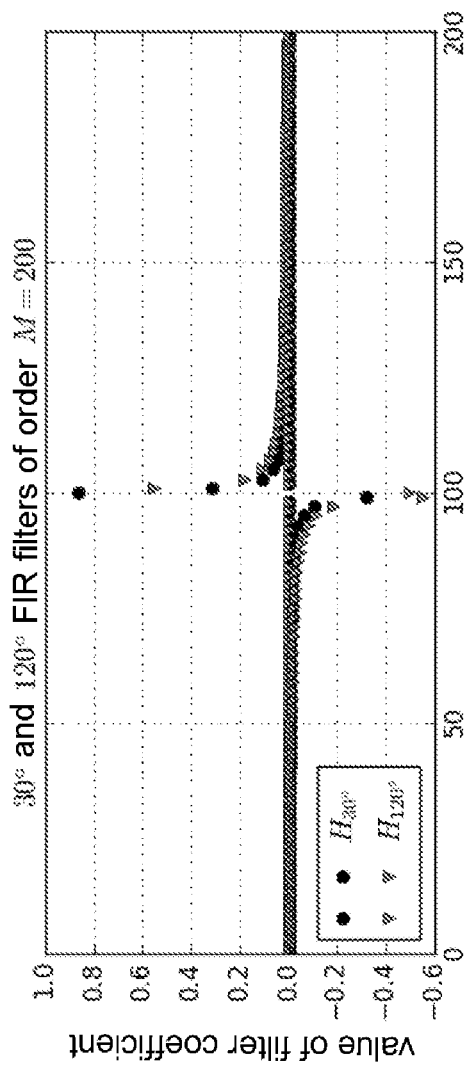
FIG. 10a shows a diagram illustrating two FIR (finite impulse response filters) $H_{30°}$ (circles) and $H_{120°}$ (triangles), for the invention, with the value of the filter coefficients plotted upward and the number of the filter coefficients plotted toward the right.
Figure 10B:
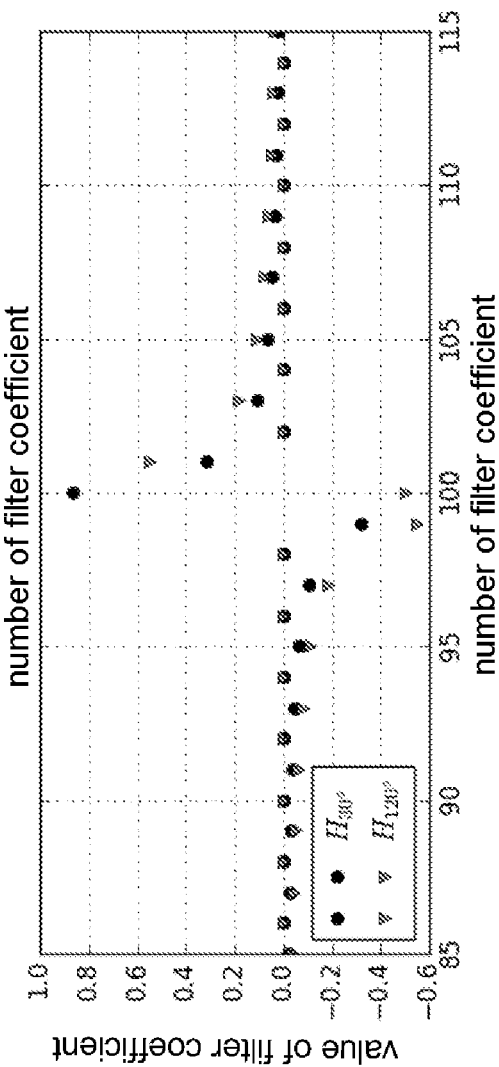
FIG. 10b shows an extract from the diagram from FIG. 10a, in the region around the number of the filter coefficient k=100.

The application of the phase splitter described above is demonstrated analogously to the previous example. For this purpose, two FIR filters $H_1=H_{30°}$ and $H_2=H_{120°}$ of the order M=200 were constructed, said filters respectively causing a phase shift of 30° and 120° and thus having a phase difference of 90° with respect to one another. The filter coefficients $H_{30°}(k)$ (circles) and $H_{120°}(k)$ (triangles) of the impulse responses of the 30° and 120° FIR filters, for use as a phase splitter, are illustrated in FIG. 10a and in an enlarged extract around the region k=100 in FIG. 10b. It is evident that, analogously to the Hilbert transformer $H_{90°}$ above, every second filter coefficient of $H_{30°}$ and $H_{120°}$ is equal to zero.

Both filters are in each case applied to the data set from FIG. 3 in accordance with equation (11); the result of the

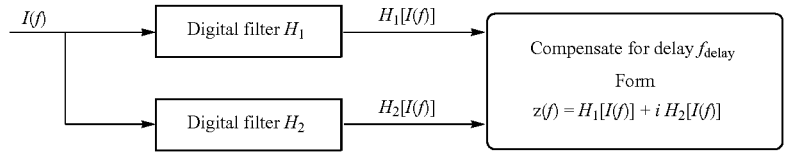

application and the calculated instantaneous envelope A(f) are illustrated in FIGS. 11a-11d. The application to the original measurement data I(f) (illustrated in FIG. 11a) generates two delayed curves phase-shifted by 30° (illustrated in a dashed fashion) and 120° (illustrated in a solid fashion) (cf. FIG. 11b). In order to remove the delay, both curves are shifted by the frequency $f_{delay}$ (see FIG. 11c). The instantaneous envelope S(f) is calculated as absolute value $|z(f)|$ of the analytical signal $z(f)=H_{30°}\cdot[I(f+f_{delay})]+i\cdot H_{120°}\cdot[I(f+f_{delay})]$ (see FIG. 11d).

Figure 11A:
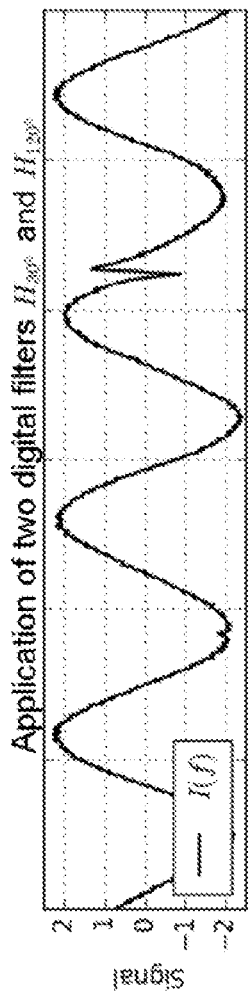
FIG. 11a shows a diagram of a THz absorption measurement, illustrating upward the measurement signal (photocurrent) I(f) as a function of the frequency f plotted toward the right.
Figure 11B:
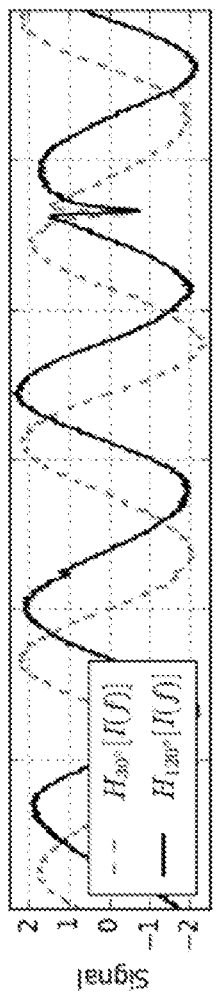
FIG. 11b shows the diagram from FIG. 11a, after application of the FIR filters $H_{30°}$ and $H_{120°}$ to I(f), according to the invention.
Figure 11C:
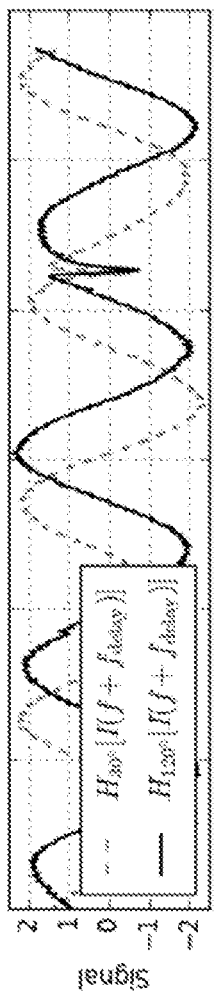
FIG. 11c shows the diagram from FIG. 11a, after application of the FIR filters $H_{30°}$ and $H_{120°}$ to the measurement signal $I(f+f_{delay})$ with phase shift $f_{delay}$, according to the invention.
Figure 11D:
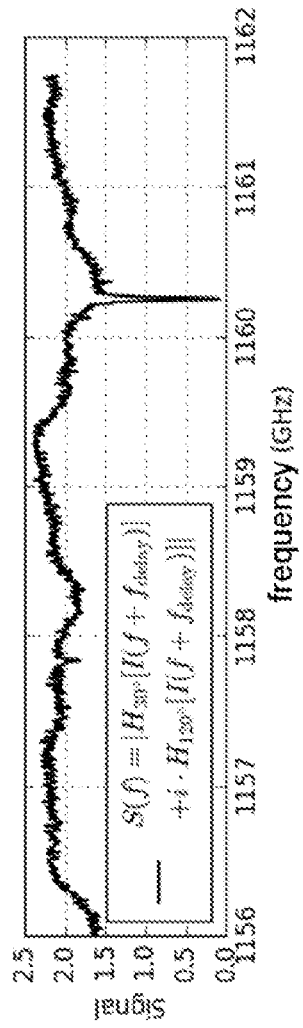
FIG. 11d shows the diagram from FIG. 11a, after the determination of the spectrum $S(f)=|H_{30°}[I(f+f_{delay})]+i\cdot H_{120°}[I(f+f_{delay})]|$, according to the invention.

In a similar manner to the previous example (cf. FIG. 9d), it is evident in FIG. 11d that with the use of $H_{30°}$ and $H_{120°}$, too, the amplitude curve A(f) can be reconstructed with high accuracy. Once again, no significant deviations are found in a direct comparison with the variant shown above (using the Fourier transformation).

To summarize, the invention relates to a method for measuring and determining a THz spectrum of a sample (17),
wherein two laser beams (1a, 2a) are superimposed, such that two parts (11, 12) of a superimposed laser radiation are generated, which have a beat frequency in the THz range,
wherein the first part (11) is introduced into an emitter (13) for generating a THz radiation (14), wherein the THz radiation (14) passes through the sample (17) and the characteristic transmission radiation (18) thus obtained is forwarded to a detector (15), wherein the detector (15) is activated by the second part (12) of the superimposed laser radiation,
wherein, by repetition with different beat frequencies, a measurement signal I(f) of the form $I(f)=A(f)\cdot\cos[\Phi(f)]$ is obtained for the sample (17),
wherein an auxiliary signal $\tilde{I}(f)$ shifted by 90° is determined from the measurement signal I(f), with $\tilde{I}(f)=A(f)\cdot\cos[\Phi(f)\pm90°]$,
and wherein the THz spectrum S(f) of the sample (17) is determined by means of the auxiliary signal $\tilde{I}(f)$, with $S(f)=|z(f)|=|I(f)+i\tilde{I}(f)|$. The invention provides a method for measuring and determining a THz spectrum in which an improved spectral resolution can be achieved in a simple manner.

LITERATURE LIST

[1] Roggenbruck A. et. al, *J. Opt. Soc. Am. B* 29 (4), 614 (2012)
[2] Roggenbruck A. et. al, *New J. Phys.* 12, 043017 (2010).

The invention claimed is:
1. A method for measuring and determining a THz spectrum of a sample, comprising
a) generating a first laser beam having a frequency $f_1$ and a second laser beam having a frequency $f_2$, with $f_2>f_1$ and with $f_1$, $f_2$ in the visible or near-infrared spectral range, wherein both laser beams are superimposed in a beam splitter having two outputs, for forming a superimposed laser radiation having a beat frequency $fs=f_2-f_1$ in the THz range and said superimposed laser radiation is available at the two outputs of the beam splitter,
b) converting a first part of the superimposed laser radiation behind a first of the outputs of the beam splitter at an emitter into THz radiation and transmitting said THz radiation through a sample, as a result of which a characteristic transmission radiation is obtained,
c) radiating the characteristic transmission radiation onto a detector, whose sensitivity is determined by a second part—radiated onto the detector—of the superimposed laser radiation behind a second of the outputs of the beam splitter, such that a measurement value I(fs) is obtained at the detector,
d) repeating steps a) to c) a number of times with n different beat frequencies fs, such that a discrete frequency-dependent measurement signal I(f) is obtained, wherein the measurement signal I(f) is of the form $I(f)=A(f)\cdot\cos[\Phi(f)]$ with A(f): amplitude term, and $\Phi(f)$: phase term,
e) determining an auxiliary signal $\tilde{I}(f)$ shifted shifted by 90° from the measurement signal I(f), with $\tilde{I}(f)=A(f)\cdot\cos[\Phi(f)\pm90°]$,
f) determining the THz spectrum S(f) by means of the auxiliary signal $\tilde{I}(f)$, with $S(f)=|z(f)|=|I(f)+i\tilde{I}(f)|$.

2. The method as claimed in claim 1, wherein in step e) the auxiliary signal $\tilde{I}(f)$ is determined from the measurement signal I(f) by applying a Hilbert transformation, with $\tilde{I}(f)=H[I(f)]$.

3. The method as claimed in claim 1 or 2, wherein in step e) the following substeps are applied:
i) applying a complex Fourier transformation to the measurement signal I(f), such that a transformed measurement signal I(t) in the time domain is obtained,
ii) applying a filter function to the transformed measurement signal I(t), such that a filtered transformed measurement signal GEF[I(t)] is obtained,
iii) applying the inverse complex Fourier transformation to the filtered transformed measurement signal GEF[I(t)], such that a complex inverse-transformed measurement signal RUC(f) is obtained, the imaginary part of which is used as $\tilde{I}(f)$.

4. The method as claimed in claim 3, wherein a vector h of the length n is used as filter function, with
a. $h_i=1$ for i=1 and for $$i = \frac{n}{2} + 1$$

b. $h_i=2$ for $$i = 2, 3, \ldots, \frac{n}{2}$$

c. $h_i=0$ for $$i = \frac{n}{2} + 2, \ldots, n$$

for n even, and
a'. $h_i=1$ for i=1 and for i=n/2+½
b'. $h_i=2$ for $$i = 2, 3, \ldots, \frac{n}{2} - 1/2$$

c'. $h_i=0$ for i=n/2+3/2, . . . , n
for n odd,
wherein the vector h is multiplied element by element by the transformed measurement signal I(t).

5. The method as claimed in claim 1 or 2, wherein in step e) the auxiliary signal $\tilde{I}(f)$ is approximately determined by means of a digital filter, wherein the digital filter is applied step by step in each case only to a continuous portion of the measurement values of the measurement signal I(f), in order to determine a respective individual value of the auxiliary signal $\tilde{I}(f)$ whose frequency is contained in the continuous portion of the measurement values.

6. The method as claimed in claim 1 or 2, wherein in step e), instead of $\tilde{I}(f)$ a z(f) is approximately determined as $H_1[I(f)]+iH_2[I(f)]$, wherein $H_1$, $H_2$ are digital filters, wherein the digital filters are applied step by step in each case only to an identical, continuous portion of the measurement values of the measurement signal I(f), in order to determine a respective individual value of z(f) whose frequency occurs in the continuous portion of the measurement values, with $H_1[I(f)]=A(f)\cdot\cos[\Phi(f)+\alpha]$ and $H_2[I(f)]=A(f)\cdot\cos[\Phi(f)\pm 90°+\alpha]$, with $\alpha$: phase offset of the digital filterings, and wherein in step f) determining the THz spectrum S(f) is carried out not by means of the auxiliary signal $\tilde{I}(f)$, but rather with $S(f)=|z(f)|=|H_1[I(f)]+iH_2[I(f)]|$.

7. The method as claimed in claim 1 or 2, wherein
a THz reference spectrum $S_0(f)$ is measured and determined analogously to steps a) to f) but without a sample (17);
and the THz spectrum S(f) of the sample (17) is divided element by element by the THz reference spectrum $S_0(f)$, such that a transmission spectrum $$T(f) = \frac{S(f)}{S_o(f)}$$

is obtained.

8. The method as claimed in claim 7, wherein an absorbance Abs(f) is calculated from the transmission spectrum T(f) by forming the negative common logarithm, with:
$Abs(f)=-\log_{10}(T(f))$.

9. The method as claimed in claim 1 or 2, wherein
$I_0(f)$ and $\tilde{I}_0(f)$ are measured and determined analogously to steps a) to e), but without a sample;
and given a known sample thickness d the real part of the refractive index n(f) of the sample is determined, as a function of the frequency f, comprising the following steps:
calculating the phase $$\varphi(f) = \arctan\left(\frac{\tilde{I}(f)}{I(f)}\right)$$

for all frequency points of the variables I(f) and $\tilde{I}(f)$, determined with sample,
calculating the phase $$\varphi_0(f) = \arctan\left(\frac{\tilde{I}_0(f)}{I_0(f)}\right)$$

for all frequency points of the variables $I_0(f)$ and $\tilde{I}_0(f)$, determined without sample;

calculating the phase difference $\Delta\varphi(f)=\varphi(f)-\varphi_0(f)$ for all frequencies f, and subsequently calculating the real part of the refractive index n(f) by applying the following formula:

$$n(f) = \frac{\Delta\varphi(f)\cdot c}{2\pi df}$$

with the speed of light c.

10. The method as claimed in claim 1 or 2, wherein $I_0(f)$ and $\tilde{I}_0$ are measured and determined analogously to steps a) to e), but without a sample;
and given a known real part n(f) of the refractive index of the sample, the sample thickness d is determined, comprising the following steps:
calculating the phase $$\varphi(f) = \arctan\left(\frac{\tilde{I}(f)}{I(f)}\right)$$

for all frequency points of the variables I(f) and $\tilde{I}(f)$ determined with sample;
calculating the phase $$\varphi_0(f) = \arctan\left(\frac{\tilde{I}_0(f)}{I_0(f)}\right)$$

for all frequency points of the variables $I_0(f)$ and $\tilde{I}_0(f)$, determined without sample;
calculating the phase difference $\Delta\varphi(f)=\varphi(f)-\varphi_0(f)$ for all frequencies f;
applying the formula $$d(f) = \frac{\Delta\varphi(f)\cdot c}{2\pi n(f)f}$$

to the frequency points f, and averaging the variable d(f) over all frequencies f in order to obtain the sample thickness $d=\overline{d(f)}$.

11. The method as claimed in claim 1 or 2, wherein information about a qualitative and/or quantitative composition of the sample is determined from the THz spectrum S(f) of the sample and/or from the transmission spectrum T(f) and/or from the absorbance Abs(f).

12. The method as claimed in claim 1, wherein:
the beam splitter is a fiber-based beam splitter, and
the discrete frequency-dependent measurement signal I(f) is obtained at the beat frequencies $f[k]=k\cdot\delta f+f_0$, with $k=1,\ldots,n$ and $f_0$: starting frequency.

* * * * *